US010274438B2

United States Patent
Mashita et al.

(10) Patent No.: US 10,274,438 B2
(45) Date of Patent: Apr. 30, 2019

(54) METHOD FOR OBSERVING DEFORMATION OF ELASTIC MATERIAL AND APPARATUS FOR CAPTURING PROJECTION IMAGE OF ELASTIC MATERIAL

(71) Applicant: SUMITOMO RUBBER INDUSTRIES, LTD., Kobe-shi, Hyogo (JP)

(72) Inventors: Ryo Mashita, Kobe (JP); Hiroyuki Kishimoto, Kobe (JP)

(73) Assignee: SUMITOMO RUBBER INDUSTRIES, LTD., Kobe-shi, Hyogo (JP)

( * ) Notice: Subject to any disclaimer, the term of this patent is extended or adjusted under 35 U.S.C. 154(b) by 201 days.

(21) Appl. No.: 15/036,634

(22) PCT Filed: Nov. 6, 2014

(86) PCT No.: PCT/JP2014/079419
§ 371 (c)(1),
(2) Date: May 13, 2016

(87) PCT Pub. No.: WO2015/072387
PCT Pub. Date: May 21, 2015

(65) Prior Publication Data
US 2016/0282286 A1    Sep. 29, 2016

(30) Foreign Application Priority Data

Nov. 15, 2013 (JP) .................. 2013-237157
Jun. 26, 2014 (JP) .................. 2014-131683

(51) Int. Cl.
*G01B 15/06*    (2006.01)
*G01M 17/03*    (2006.01)
(Continued)

(52) U.S. Cl.
CPC ........... *G01N 23/046* (2013.01); *G01B 15/06* (2013.01); *G01M 17/027* (2013.01);
(Continued)

(58) Field of Classification Search
CPC ....... G01N 2223/401; G01N 2223/419; G01N 2223/627; G01B 15/06; G01M 17/028
See application file for complete search history.

(56) References Cited

U.S. PATENT DOCUMENTS 3,807,226 A * 4/1974 Williams ............ G01M 17/027
250/338.1
3,826,919 A * 7/1974 Yaroshuk ............. G01N 23/185
378/196

(Continued)

FOREIGN PATENT DOCUMENTS

| EP | 1136807 A2 | 9/2001 |
| EP | 2353890 A1 | 8/2011 |
| EP | 2568284 A2 | 3/2013 |

OTHER PUBLICATIONS

Extended European Search Report, dated May 30, 2017, for European Application No. 14862786.2.

*Primary Examiner* — David J Makiya
*Assistant Examiner* — Soorena Kefayati
(74) *Attorney, Agent, or Firm* — Birch, Stewart, Kolasch & Birch, LLP

(57) ABSTRACT

A method for observing deformation of an elastic material including rubber or elastomer, includes a first step of capturing projection images of at least a part of the elastic material from directions perpendicular to an arbitrary axis of the elastic material and a second step of constructing a three-dimensional image of the elastic material from the projection images. The first step includes deforming the elastic material in predetermined constant cycles, outputting capture signals at the same time points of the predetermined (Continued)

constant cycles, and capturing the projection images based on the respective capture signals.

21 Claims, 21 Drawing Sheets

(51) Int. Cl.
  *G01N 23/04* (2018.01)
  *G01N 23/046* (2018.01)
  *G01M 17/02* (2006.01)
(52) U.S. Cl.
  CPC .......... *G01M 17/028* (2013.01); *G01N 23/04* (2013.01); *G01N 2223/401* (2013.01); *G01N 2223/419* (2013.01); *G01N 2223/627* (2013.01)

(56) References Cited

U.S. PATENT DOCUMENTS

| | | | | |
|---|---|---|---|---|
| 3,883,744 A * | 5/1975 | Steffel | ................... | G01N 23/185 378/61 |
| 4,785,354 A * | 11/1988 | Nakamura | .......... | G01M 17/028 378/20 |
| 4,813,062 A * | 3/1989 | Gilpatrick | ............... | A61F 13/44 250/302 |
| 4,839,914 A * | 6/1989 | Curry | ................... | G01M 17/028 378/56 |
| 5,861,454 A * | 1/1999 | Ikeda | ........................ | B60C 1/00 524/495 |
| 5,917,876 A * | 6/1999 | Fujii | ................... | G01M 17/028 378/4 |
| 6,274,662 B1 * | 8/2001 | Lynch | ...................... | C08K 9/06 523/209 |
| 6,735,278 B2 * | 5/2004 | Madsen | ................. | G01N 23/20 378/71 |
| 6,840,097 B1 * | 1/2005 | Huber | .................... | G01B 11/30 356/237.1 |
| 9,029,779 B2 * | 5/2015 | Estor | ...................... | G01N 21/95 250/341.6 |
| 9,341,546 B2 * | 5/2016 | Stuke | .................. | G01M 17/013 |
| 9,702,833 B2 * | 7/2017 | Decroux | .............. | G01N 23/185 |
| 2005/0254856 A1 * | 11/2005 | Miura | ................ | G03G 21/0011 399/159 |
| 2014/0050305 A1 * | 2/2014 | Zhao | ...................... | G01N 23/04 378/141 |
| 2014/0324401 A1 * | 10/2014 | Kishimoto | .............. | C08L 21/00 703/2 |
| 2015/0098547 A1 * | 4/2015 | Wakasaya | ............ | G01N 23/083 378/51 |
| 2015/0377802 A1 * | 12/2015 | Decroux | ............ | G01N 23/185 378/61 |

* cited by examiner

METHOD FOR OBSERVING DEFORMATION OF ELASTIC MATERIAL AND APPARATUS FOR CAPTURING PROJECTION IMAGE OF ELASTIC MATERIAL

TECHNICAL FIELD

The present invention relates to a method for observing an elastic material under dynamically deformed state, and an apparatus for capturing a projection image of the elastic material suitably used for that purpose.

BACKGROUND ART

In the following Patent Document 1, there has been disclosed an observing method for obtaining an image relating to an interior of a friction material by transmitting radiation light through the interior of the friction material. This method, however, does not teach to observe a deformed state at a time point when the deformation of the friction material is periodical for example.
Patent Document 1: Japanese Unexamined Patent Publication No. 2009-85732

DISCLOSURE OF THE INVENTION

Problems to be Solved by the Invention

The present invention was made in view of the circumstances as described above, and a main object is to provide an observing method capable of observing a particular deformed state (deformation moment) of a periodically deformed elastic material, and an apparatus for capturing a projection image of the elastic material suitably used for that purpose.

Means for Solving the Problems

The present invention is a method for observing a deformation of an elastic material including rubber or elastomer, comprises
a projection image obtaining step of capturing a projection image of at least a part of the elastic material, from a direction perpendicular to an arbitrary axis of the elastic material, at a plurality of capture positions around the axis,
a three-dimensional image constructing step of constructing a three-dimensional image of the elastic material from the projection images, and
a step of observing the three-dimensional image, and is characterized in that
the projection image obtaining step comprises
a deforming step of deforming the elastic material in predetermined cycles,
a signal output step of outputting an capture signal at a predetermined specific time point during one cycle, and
a capturing step for capturing the projection image of the elastic material based on the capture signal, and
the deforming step, the signal output step and the capturing step are performed at each of the capture positions.

In the method for observing a deformation of an elastic material according to the present invention, it is preferable that the deforming step comprises a step of linearly reciprocating the elastic material while being pressed onto a contacted surface.

In the method for observing a deformation of an elastic material according to the present invention, it is preferable that the signal output step comprises a step of outputting the capture signal by detecting a specific position in the linear reciprocating motion of the elastic material.

In the method for observing a deformation of an elastic material according to the present invention, it is preferable to further comprise a step of preparing the elastic material whose outer peripheral surface is formed into a circular shape, and the deforming step comprises a step of rotating the circular outer peripheral surface of the elastic material while pressing onto the contacted surface.

In the method for observing a deformation of an elastic material according to the present invention, it is preferable that the deforming step comprises a step of setting a slip angle on the elastic material.

In the method for observing a deformation of an elastic material according to the present invention, it is preferable that the signal output step comprising a step of outputting the capture signal by detecting a specific position of the elastic material during rotating.

In the method for observing a deformation of an elastic material according to the present invention, it is preferable that the capturing step comprises a step of capturing the projection image including at least part of the contact portion between the elastic material and the contacted surface onto which the elastic material is pressed.

In the method for observing a deformation of an elastic material according to the present invention, it is preferable that the deforming step further comprises a step of supplying a fluid between the elastic material and the contacted surface onto which the elastic material is pressed.

The present invention is an apparatus for deforming an elastic material including rubber or elastomer and capturing a projection image of the elastic material, and preferably comprises
a deforming means for deforming the elastic material in predetermined cycles by pressing it onto a contacted surface,
a contact base having the contacted surface,
a capture signal outputting means for outputting an capture signal at a predetermined specific time point during one cycle, and
a capturing means for capturing a projection image of at least a part of the elastic material, from a direction perpendicular to an arbitrary axis of the elastic material, at a plurality of capture positions around the axis, based on the capture signal.

In the apparatus for capturing a projection image of an elastic material according to the present invention, it is preferable that the deforming means comprises a first pusher to make the elastic material linearly reciprocate while pressing onto the contacted surface.

In the apparatus for capturing a projection image of an elastic material according to the present invention, it is preferable that the first pusher includes
a electric motor having an output shaft that rotates,
a conversion device for converting the rotational motion of the output shaft to a linear reciprocating motion, and
a holder for holding the elastic material, connected to the conversion device.

In the apparatus for capturing a projection image of an elastic material according to the present invention, it is preferable that the capture signal outputting means comprises a position detecting device for detecting a specific position in the linear reciprocating motion of the elastic material, and a pulse generator for outputting a pulse signal based on a detection signal of the position detecting device.

In the apparatus for capturing a projection image of an elastic material according to the present invention, it is preferable that the elastic material has a circular outer peripheral surface, and
the deforming means includes a second pusher for rotating the outer circumferential surface of the elastic material while pressing onto the contacted surface.

In the apparatus for capturing a projection image of an elastic material according to the present invention, it is preferable that the second pusher comprises a holder for holding the elastic material, a first rotating means for rotating the elastic material, and an adjuster for changing the distance between the holder and the contacted surface.

In the apparatus for capturing a projection image of an elastic material according to the present invention,
it is preferable to further comprise a slip angle setting means for setting a slip angle on the elastic material to rotate on the contacted surface.

In the apparatus for capturing a projection image of an elastic material according to the present invention, it is preferable that the contact base comprises a cylindrical drum, and the contacted surface is formed in the outer peripheral surface of the drum.

In the apparatus for capturing a projection image of an elastic material according to the present invention, it is preferable that a simulated road surface is formed in the contacted surface.

In the apparatus for capturing a projection image of an elastic material according to the present invention, the contact base further comprises a second rotating means for moving the contacted surface.

In the apparatus for capturing a projection image of an elastic material according to the present invention, it is preferable that the capture signal outputting means comprises a first rotational position detecting device for detecting a specific position of the elastic material during rotating, a second rotational position detecting device for detecting a specific position of the contacted surface during moving, and a pulse generator for outputting a pulse signal based on a detection signal of the first rotational position detection device and a detection signal of the second rotational position detecting device.

In the apparatus for capturing a projection image of an elastic material according to the present invention, it is preferable that the capturing means comprises an x-ray camera having a shutter trigger, and the capture signal is input to the shutter trigger.

In the apparatus for capturing a projection image of an elastic material according to the present invention, it is preferable to further comprises a fluid supply means for supplying a fluid to a contact portion between the elastic material and the contacted surface.

In the apparatus for capturing a projection image of an elastic material according to the present invention, it is preferable that the elastic material contains marker particles.

Effect of the Invention

The invention as set forth in claim 1 includes the projection image obtaining step of capturing the projection image of at least a part of the elastic material, from the direction perpendicular to the arbitrary axis of the elastic material, at the capture positions around the axis, the three-dimensional image constructing step of constructing the three-dimensional image of the elastic material from the projection images, and the step of observing the three-dimensional image.

The projection image obtaining step comprises the deforming step of deforming the elastic material in the predetermined cycles, the signal output step of outputting the capture signal at the predetermined specific time point during one cycle, and the capturing step for capturing the projection image of the elastic material based on the capture signal. The deforming step, the signal output step and the capturing step are performed at each of the capture positions.

Thus, according to the invention as set forth in claim 1, even when the elastic material is deformed periodically, always the projection images under the specific state of deformation (deformation moment) are obtained at a plurality of the positions. Accordingly, it becomes possible to observe an elastic material by constructing a three-dimensional image in a specific state of deformation, The invention as set forth in claim 9 comprises the contact base having the contacted surface onto which the elastic material is pressed, the deforming means for deforming the elastic material in the predetermined cycles, the capture signal outputting means for outputting the capture signal at the predetermined specific time point during one cycle, and the capturing means for capturing the projection image of at least a part of the elastic material, from the direction perpendicular to the arbitrary axis of the elastic material, at the capture positions around the axis, based on the capture signal.

Therefore, according to the invention as set forth in claim 9, even when the elastic material is periodically deformed, always the projection images under the specific state of deformation (deformation moment) are obtained at a plurality of the positions.
The three-dimensional image of the elastic material can be constructed by using these projection images.

Figure 1:
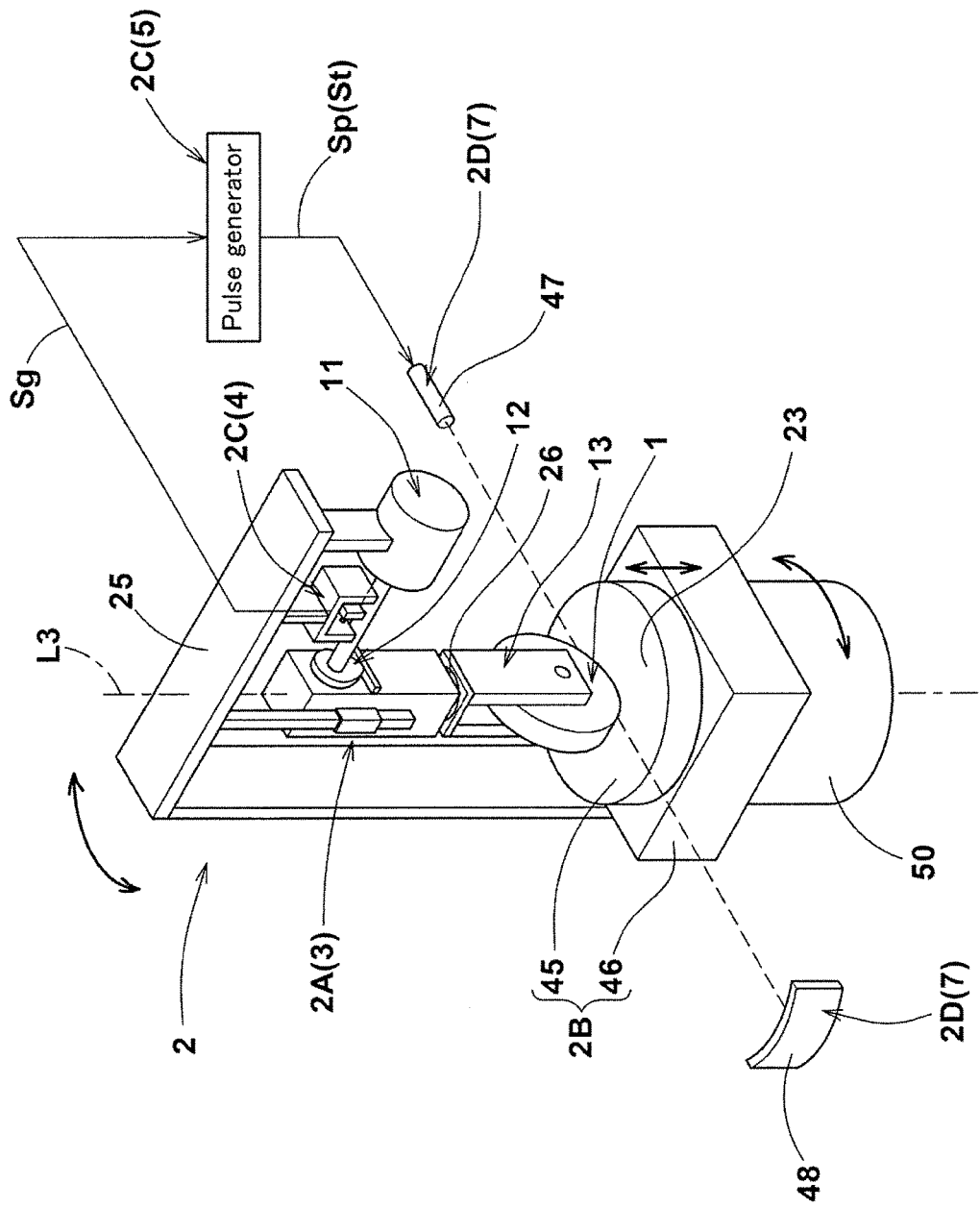
FIG. 1 A perspective view of an apparatus for capturing a projection image of the elastic material according to the present embodiment.

DESCRIPTION OF THE REFERENCE CHARACTERS 1 elastic material
51 three-dimensional image
Sg3 capture signal
P capture position

BEST MODE FOR CARRYING OUT THE INVENTION

Hereinafter, an embodiment of the present invention will be described with reference to the accompanying drawings.

The method of observing the deformation of an elastic material according to the present embodiment (hereinafter, simply referred to as "observing method") is a method for observing deformation of the elastic material including containing rubber or elastomer.

The apparatus for capturing a projection image of the elastic material used in the observing method in the present embodiment (hereinafter, simply referred to as "projection image capture apparatus") is for deforming the elastic material and capturing the projection image thereof.

FIG. 1 is a perspective view of the projection image capture apparatus used in the observing method according to the present embodiment.

Figure 2:
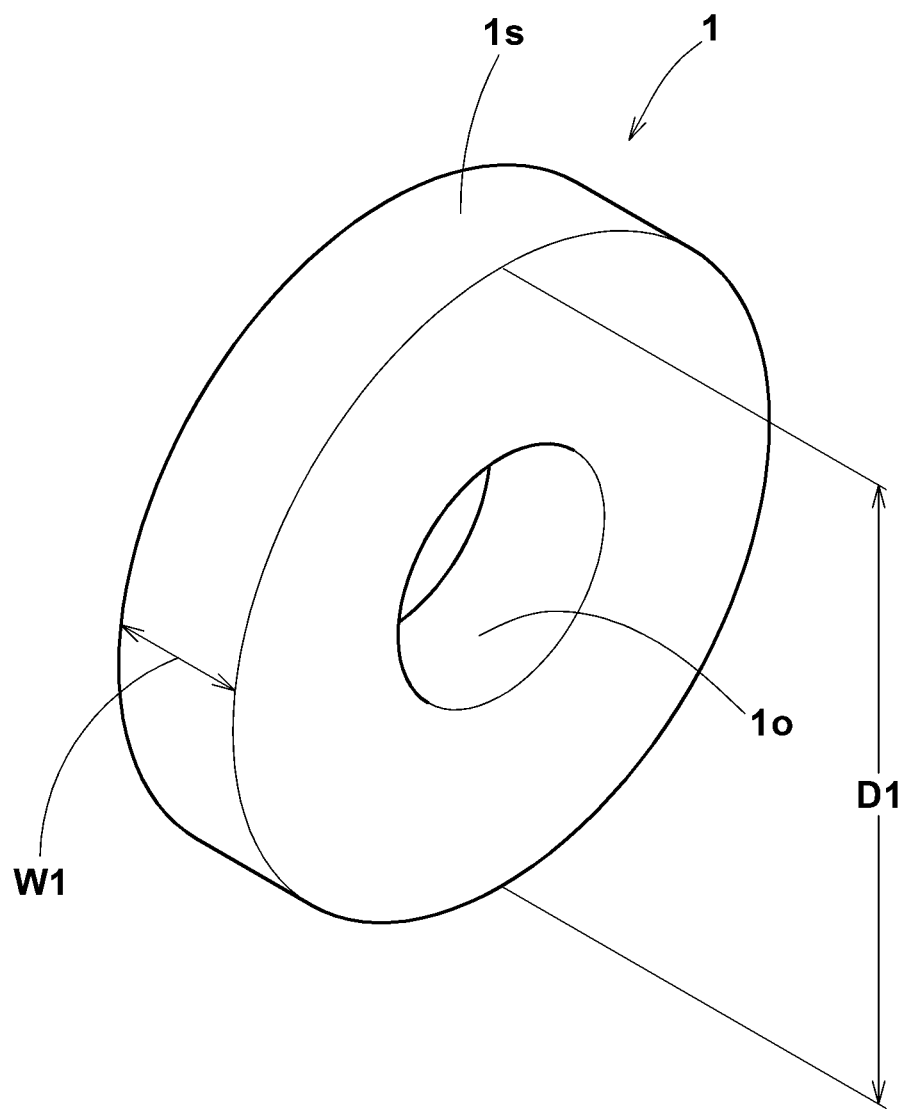
FIG. 2 A perspective view of an elastic material in the present embodiment.

FIG. 2 is a perspective view of the elastic material in the present embodiment.

As shown in FIG. 2, the elastic material 1 is, for example, formed as a cylindrical rubber material whose outer peripheral surface 1s is formed in a circular shape.

The elastic material 1 is provided in the center with a hole 1o penetrating in the thickness direction (axial direction). The outer diameter D1 of the elastic material 1 is set to be, for example, about 50 mm to 100 mm.

Further, the width W1 of the elastic material 1 is set to be, for example, about 15 mm to 30 mm.

As shown in FIG. 1, the projection image capture apparatus 2 is provided with a deforming means 2A for pressing the elastic material 1 onto a contacted surface 23, a contact base 2B having the contacted surface 23, a capture signal outputting means 2C, and a capturing means 2D.

Figure 3:
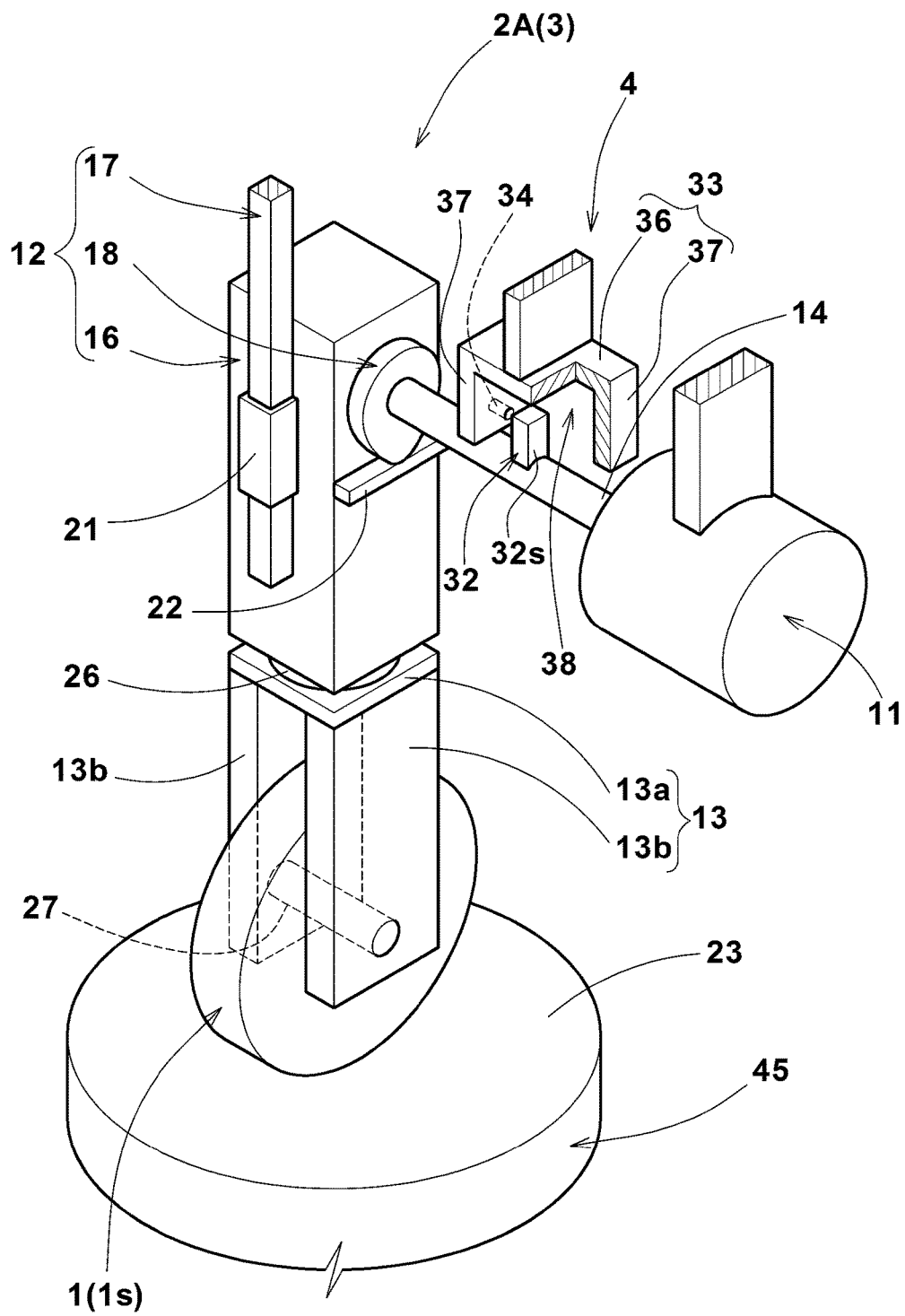
FIG. 3 An enlarged perspective view showing a first pusher.

FIG. 3 is an enlarged perspective view showing a first pusher.

The deforming means 2A is for the purpose of deforming the elastic material 1 in predetermined cycles by pressing it onto the contacted surface 23.

The deformation means 2A in the present embodiment is formed as the first pusher 3 to make the elastic material 1 linearly reciprocate.

The first pusher 3 includes an electric motor 11 having an output shaft 14 which rotates, a conversion device 12 which converts the rotational motion of the output shaft 14 to a linear reciprocating motion, and a holder 13 for holding the elastic material 1.

As the electric motor 11 in the present embodiment, for example, an AC or DC electric motor is employed.

As shown in FIG. 1, the electric motor 11 is supported by a L-shaped support frame 25 fixed to the contact base 2B.

As shown in FIG. 3, the output shaft 14 extends horizontally and is rotated about a horizontal axis by the electric motor 11.

The conversion device 12 includes a base portion 16, a rail portion 17, and a cam 18.

The base portion 16 is, for example, formed in a rectangular parallelepiped shape extending in the up-down direction.

The base portion 16 is provided on a side with a slide mechanism 21 that engages the rail portion 17.

Further, the base portion 16 is provided on the other side with a follower portion 22 extending horizontally on the lower side of the cam 18 and contacting with the outer peripheral surface of the cam 18.

By the restoring force of the elastic material 1 pressed onto the contacted surface 23, the outer peripheral surface of the follower 22 and the cam 18 are in close contact without any gap therebetween.

The rail portion 17 extends in the up-down direction on one side of the base portion 16, and its upper end is fixed to the support frame 25 (shown in FIG. 1).

By such rail portion 17, the base portion 16 can be guided in the up-down direction through the slide mechanism 21.

Figure 4:
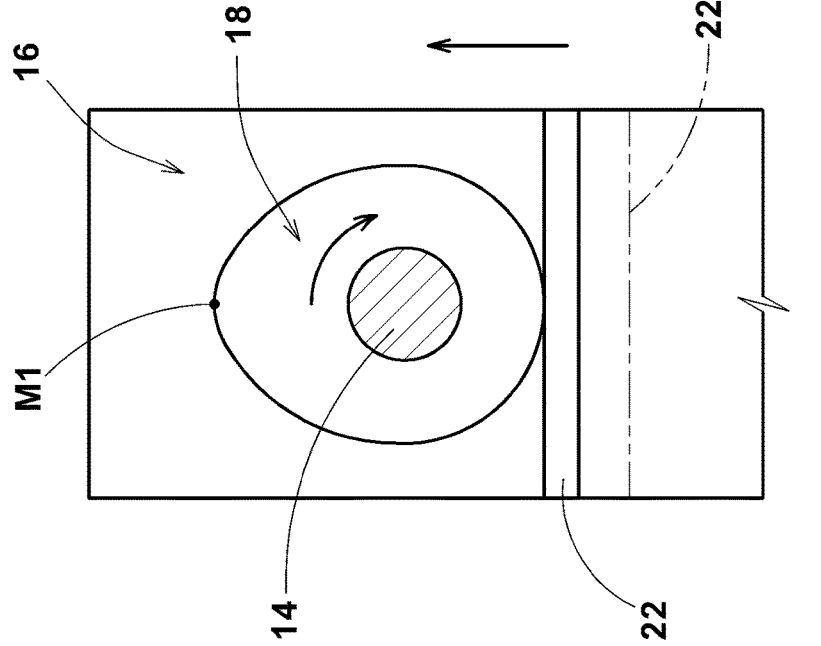
FIG. 4(a) is a side view showing a cam pressing down a base portion, and (b) is a side view showing the cam relaxing the pressing down.
Figure 4:
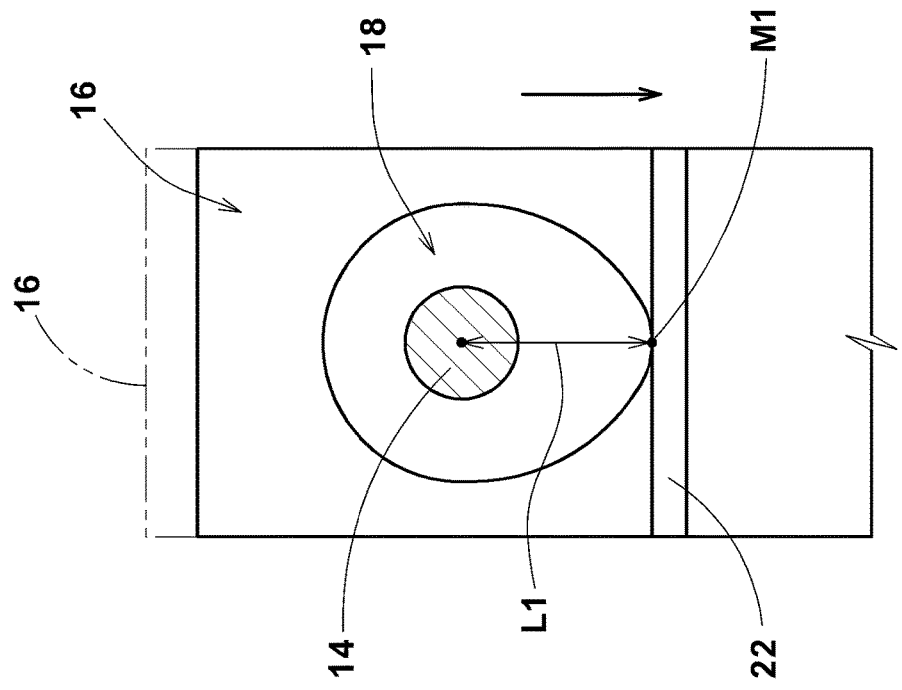

FIG. 4 is an enlarged side view showing the cam 18 and the follower portion 22.

The cam 18 is formed as a disc cam having a substantially ovoid shape whose distance L1 from its center to the outer peripheral surface is not constant.

As shown in FIGS. 3 and 4, one end of the output shaft 14 of the electric motor 11 is fixed to the center of the cam 18. Accordingly, by the rotation of the output shaft 14, the cam 18 can be rotated about a horizontal axis.

As shown in FIG. 3, the holder 13 includes a horizontal plate 13a extending horizontally, and a pair of vertical plates 13b and 13b extending downward from both ends of the horizontal plate 13a. Thus, the holder 13 is formed in a substantially u-shaped in the front view.

The upper end of the horizontal plate 13a is connected to the lower end of the base portion 16 of the conversion device 12 through a load cell 26 capable of detecting a load.

The lower end sides of a pair of the vertical plates 13b, 13b are disposed on both sides of the elastic material 1.

In addition, a pair of the vertical plates 13b, 13b are provided with a shaft portion 27 extending horizontally between a pair of the vertical plates 13b, 13b.

The shaft portion 27 is fixed to the hole 1o of the elastic material 1 (shown in FIG. 2).

Thereby, the elastic material 1 is held rotatably around the horizontal axis.

In such first pusher 3, firstly, the output shaft 14 of the electric motor 11 is rotated in a state of the elastic material 1 being pressed onto the contacted surface 23.

By the rotation of the output shaft 14, the cam 18 is rotated about a horizontal axis.

By the rotation of the cam 18, through the follower portion 22 with which the outer circumferential surface of the cam 18 contacts, the pressing down of the base portion 16 (shown in FIG. 4(*a*)) and relaxation of the pressing down (shown in to FIG. 4(*b*)) are repeated alternately.

In addition, the period in which the cam 18 makes one revolution is the same as the period in which the base portion 16 makes one reciprocating stroke. Therefore, by the conversion device 12, the rotational motion of the output shaft 14 of the electric motor 11 can be converted to cyclic linear reciprocating motion in the up-down direction.

By the linear reciprocating motion of the base portion 16 of the conversion device 12, the elastic material 1 can be linearly reciprocated in the up-down direction through the holder 13.

By such linear reciprocating motion, the compression deformation of the elastic material 1 toward the contacted surface 23 and relaxation of the compressive deformation are performed alternately. Therefore, the first pusher 3 can deform the elastic material 1 in predetermined cycles, while pressing it onto the contacted surface 23.

Incidentally, in the first pusher 3 in the present embodiment, it is configured as a vibrating device using an electric motor 11, but it is not limited thereto.

As the first pusher 3, for example, it may be configured as vibrating unit of an oil type or an electromagnetic type.

As shown in FIG. 1, the contact base 2B includes a road surface portion 45 provided in the upper surface with the contacted surface 23, and a lower supporting portion 46 for supporting the road surface portion 45.

The road surface portion 45 is formed in a plate shape which is circular in a plan view.

In the contacted surface 23, for example, a simulated road surface where irregularities of the asphalt pavement are reproduced is preferably formed.

The lower supporting portion 46 is formed in a plate shape which is rectangular in a plan view.

To the lower supporting portion 46, a bottom side of the support frame 25 is fixed.

Further, the lower supporting portion 46 is provided with a lifting means (not shown) for moving the road surface portion 45 in the up-down direction.

By the lifting means, the road surface portion 45 is moved in the up-down direction relatively to the elastic material 1. Thereby, the load to be applied to the elastic material 1 can be adjusted.

In the present embodiment, there is provided a rotating means 50 for rotating the first pusher 3 and the contacted surface 23 around the vertical axis through the support frame 25 and the lower supporting portion 46. Such rotating means 50 can move the elastic material 1 relatively to the capturing means 2D.

The capture signal outputting means 2C is for the purpose of outputting a capture signal at a predetermined specific time point within one cycle.

The capture signal outputting means 2C in the present embodiment includes the linear position detecting device 4, and the pulse generator 5.

The linear position detecting device 4 is for the purpose of detecting a specific position in the linear reciprocating motion of the elastic material 1 (specific deformed state). As the linear position detecting device 4, for example, a photo interrupter of a transmission type or a reflection type or the like can be applied.

As shown in FIGS. 1 and 3, the linear position detecting device 4 is provided with a protrusion 32 which protrudes radially outwardly from the output shaft 14, a frame 33 which is disposed above the output shaft 14, a sensor 34 for detecting the protrusion 32, and an output portion (not shown) for outputting a detection signal Sg (shown in FIG. 1).

The protrusion 32 is formed in a cubic shape having a surface 32*s* intersecting the axial direction of the output shaft 14. The outer peripheral surface of the output shaft 14 is provided with at least one protrusion 32 (one in the present embodiment). Such protrusion 32 is rotated about a horizontal axis by the rotation of the output shaft 14.

The frame 33 includes a horizontal plate 36 extending horizontally, and a pair of vertical plates 37, 37 extending from both ends of the horizontal plate 36 downwardly, and is formed in a substantially u-shaped in the front view.

Further, the frame 33 is provided with a space 38 surrounded by the horizontal plate 36 and a pair of the vertical plates 37, 37. The frame 33 is secured to the support frame 25 (shown in FIG. 1) so that the rotating protrusion 32 can pass through the space 38.

The sensor 34 is, for example, configured as a laser sensor. In the sensor 34 in the present embodiment, between a pair of the vertical plates 37, 37 of the frame 33, laser is irradiated in parallel to the axial direction of the output shaft 14. By such sensor 34, the protrusion 32 passing through the space 38 of the frame 33 can be detected. Further, when the passing of the protrusion 32 is detected, the detection signal Sg (shown in FIG. 1) is output from the output portion (not shown). The detection signal Sg is input to the pulse generator 5.

In such linear position detecting device 4, as the protrusions 32 passing through the space 38 of the frame 33 is detected by the sensor 34, a specific position of the outer peripheral surface of the output shaft 14 to which the protrusion 32 is fixed can be determined.

As shown in FIG. 4(*a*) and FIG. 4(*b*), the outer peripheral surface of the output shaft 14, and the peripheral surface of the cam 18 are rotated with the same period.

As described above, the period in which the cam 18 makes one revolution, and the period in which the base portion 16 makes one reciprocation are identical.

Therefore, in the linear position detecting device 4, as the position of the outer peripheral surface of the output shaft 14 is determined, the specific position in the linear reciprocating motion of the elastic material 1 (i.e., the specific position in the up-down direction of the elastic material 1) can be detected.

In the linear position detecting device 4, the detection signal Sg is output from the output unit (not shown) at a time point when the specific position in the linear reciprocating motion of the elastic material 1 is detected.

Incidentally, the specific position in the linear reciprocating motion of the elastic material 1 can be appropriately changed by changing the fixing position of the protrusion 32 in the circumferential direction of the output shaft 14.

As shown in FIG. 1, the pulse generator 5 is for the purpose of outputting the pulse signal Sp based on the detection signal Sg of the linear position detecting device 4. In the pulse generator 5 in the present embodiment, when the detection signal Sg of the linear position detecting device 4 is input, at least one (in the present embodiment, one) pulse signal Sp is output.

As described above, the detection signal Sg is output by the linear position detecting device 4 on the detection of the specific position in the linear reciprocating motion of the elastic material 1.

Accordingly, the pulse signal Sp is output at the specific position in the linear reciprocating motion of the elastic material 1 (specific time point in one cycle).

The output pulse signal Sp is input to the capturing means 2D as a capture signal St.

As the pulse signal Sp in the present embodiment, TTL (5V-0V) is employed, but it is not limited thereto. Other pulse signal Sp, for example, a single pulse or successive pulses may be employed.

Further, in the present embodiment, one pulse signal Sp is output by inputting the detection signal Sg, but it is not limited thereto. For example, it may be possible that successive pulse signals Sp are output during the detection signal Sg is not input, and the output of the successive pulse signals Sp is stopped only when the detection signal Sg is input.

In the capturing means 2D, an x-ray camera 7 is included. The x-ray camera 7 in the present embodiment is a conventional CT (Computed Tomography) apparatus.

The x-ray camera 7 includes an x-ray tube 47 for irradiating the elastic material 1 with x-ray, a detector 48 for detecting the x-ray transmitted through the elastic material 1, and a shutter trigger (not shown) for irradiating the x-ray from x-ray tube 47.

The x-ray tube 47 and the detector 48 are arranged in a straight line with the first pusher 3 and the contact base 2B disposed therebetween. Further, in the present embodiment, the height of the x-ray tube 47 is adjusted so that the elastic material 1 and the contacted surface 23 are irradiated with the x-ray.

The x-ray tube 47 and the detector 48 in the present embodiment are fixed immovably with respect to the first pusher 3 and the contact base 2B.

The detector 48 includes a converter (not shown) for converting x-ray into photoelectrons, a phosphor (not shown) for converting photoelectrons into visible light, and a CCD camera (not shown) for capturing a visible light like a conventional detector, When the capture signal St (pulse signal Sp) output from the pulse generator 5 is input to the shutter trigger (not shown), the x-ray from the x-ray tube 47 is irradiated for a period of 0.1 milliseconds to 100 milliseconds, for example.

Figure 5:
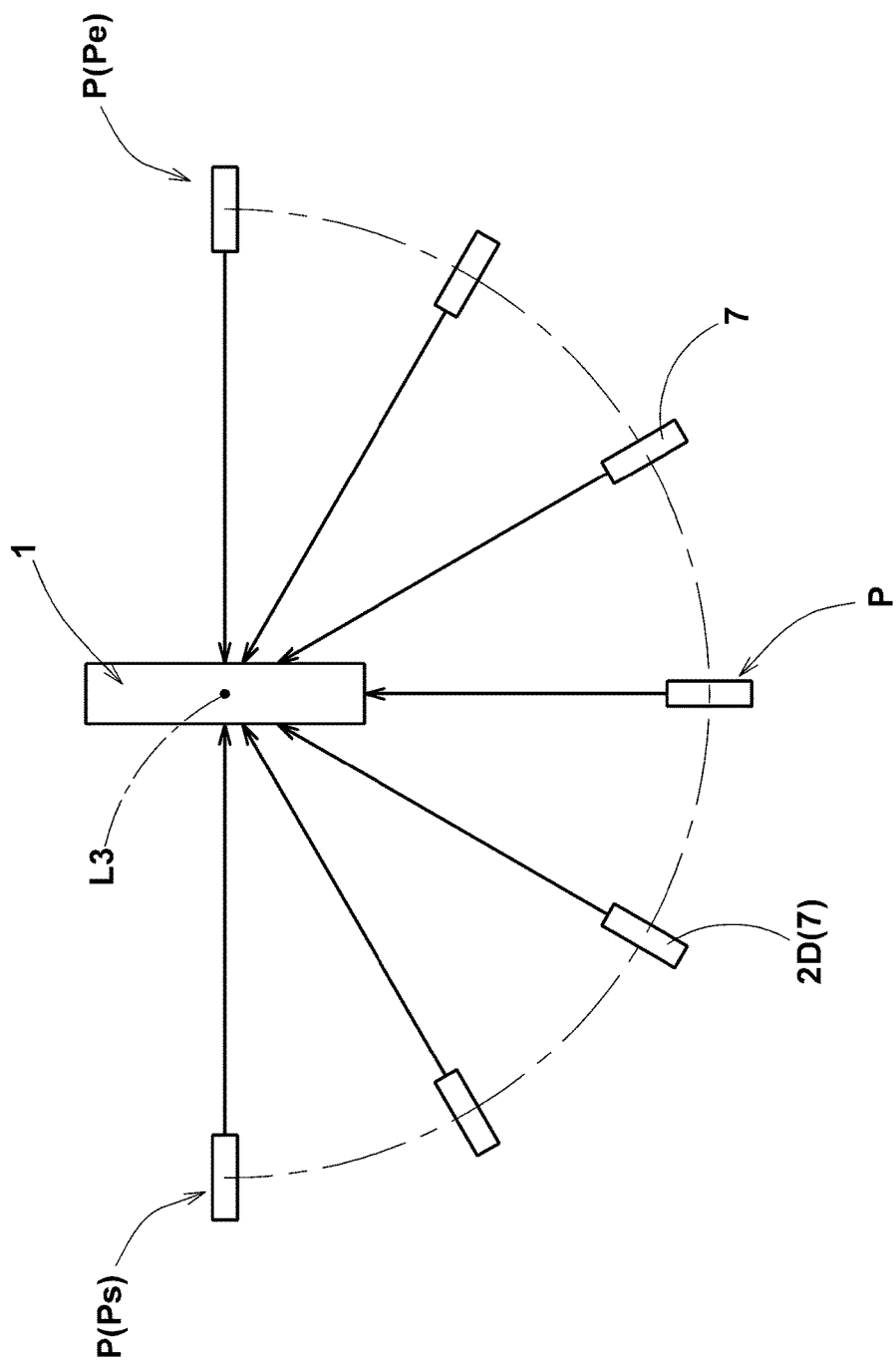
FIG. 5 A plan view showing capture positions of the elastic material.

FIG. 5 is a plan view showing a capture position P of the elastic material 1.

In the capturing means 2D, based on the capture signal St (shown in FIG. 1), the projection image of the elastic material 1 can be captured from a direction perpendicular to arbitrarily axis of the elastic material 1 (in the present embodiment, the vertical axis L3 extending vertically at the center of gravity of the elastic material 1).

Further, in the capturing means 2D, as the first pusher 3 and the contacted surface 23 are rotated around the vertical axis by the rotating means 50 shown in FIG. 1, the projection image of the elastic material 1 can be captured at a plurality of capture positions P around the axis of the elastic material.

Figure 6:
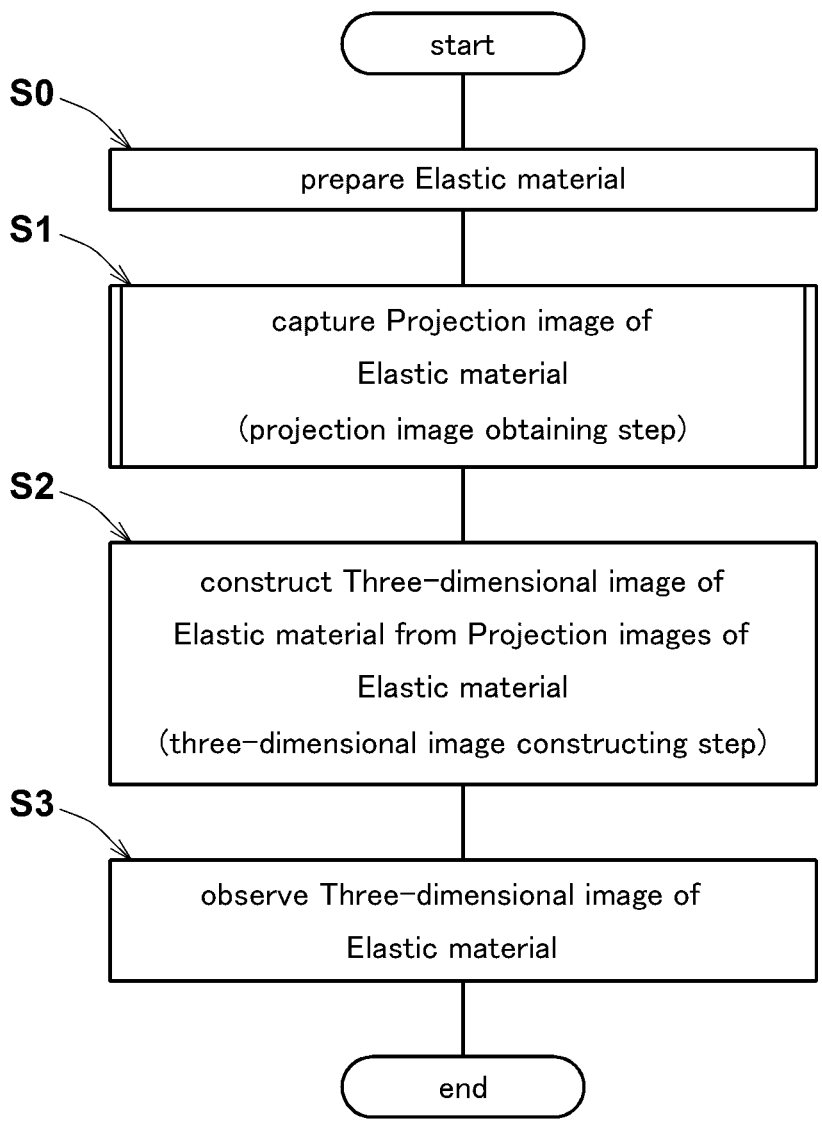
FIG. 6 A flowchart illustrating an example of the processing procedure of the observing method in the present embodiment.

Next, the observing method using the projection image capture apparatus 2 in the present embodiment is described. FIG. 6 is a flowchart illustrating an example of the processing procedure of the observing method in the present embodiment.

In the observing method in the present embodiment, first, the elastic material 1 whose outer peripheral surface is formed in a circular shape as shown in FIG. 2 is prepared (step S0).

Next, in the observing method in the present embodiment, the projection image of the elastic material 1 is captured (projection image obtaining step S1).

In the projection image obtaining step S1, as shown in FIG. 1, the projection image of at least a part of the elastic material 1 is captured at a plurality of capture positions P (shown in FIG. 5) around the axis (in the present embodiment, the vertical axis L3) from a direction perpendicular to the axis of the elastic material 1.

As shown in FIG. 5, the capture position P in the present embodiment is set at a plurality of positions at predetermined intervals around the vertical axis L3 of the elastic material 1 between a capture start position Ps on one side of the elastic material 1 and a capture end position Pe on the other side of the elastic material 1.

In the present embodiment, as the first pusher 3 and the contact base 2B are rotated around the vertical axis by the rotation of the rotating means 50, the x-ray camera 7 is positioned at a plurality of the capture positions P.

Incidentally, with reference to the vertical axis L3 of the elastic material 1, the angle (narrow angle) formed between the capture start position Ps and the capture end position Pe is preferably set to be not more than 180 degrees.

Figure 7:
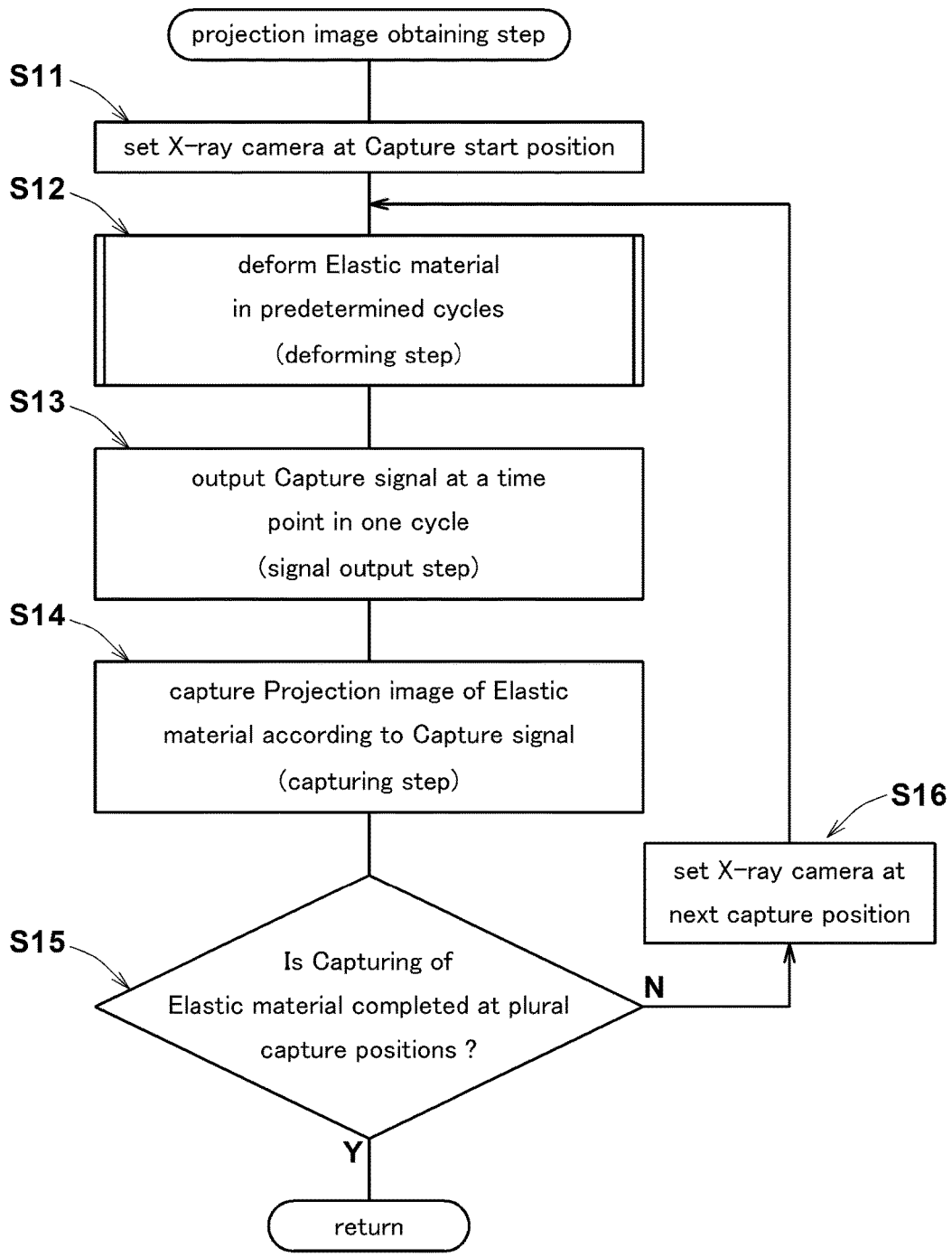
FIG. 7 A flowchart illustrating an example of the processing procedure of the capturing step in the present embodiment.

FIG. 7 is a flowchart illustrating an example of the processing procedure of the projection image obtaining step S1 in the present embodiment.

In the projection image obtaining step S1 in the present embodiment, first, the x-ray camera 7 is positioned at the capture start position Ps (shown in FIG. 5) (step S11).

In the step S11 in the present embodiment, the first pusher 3 and the contact base 2B shown in FIG. 1 are rotated around the vertical axis, and the x-ray camera 7 is arranged at the capture start position Ps.

Next, in the projection image obtaining step S1 in the present embodiment, the elastic material 1 is deformed in the predetermined cycles (deforming step S12).

Figure 8:
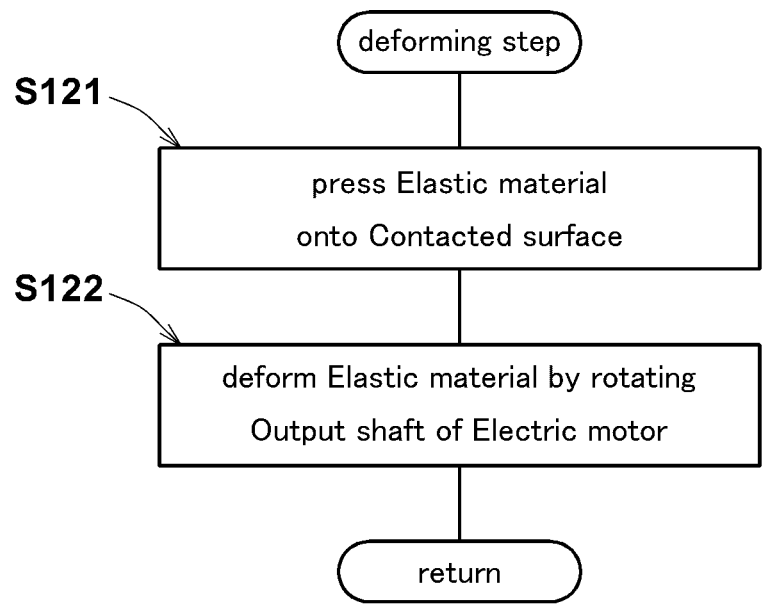
FIG. 8 A flowchart illustrating an example of the processing procedure of the deforming step in the present embodiment.

In the deformation step S12, the first pusher 3 is used. FIG. 8 is a flowchart illustrating an example of the processing procedure of the deforming step S12 in the present embodiment.

In the deforming step S12 in the present embodiment, first, as shown in FIGS. 1 and 3, the elastic material 1 is pressed onto the contacted surface 23 (step S121).

In the step S121, as shown in FIG. 4(a), a position M1 at which the above-mentioned distance L1 of the cam 18 becomes maximum (hereinafter, simply referred to as "maximum distance position of the cam") is set to the lowest point of the cam 18. Next, as shown in FIG. 1, the road surface portion 45 is moved in the up-down direction. Thereby, the elastic material 1 is pressed onto the contacted surface 23 (shown in FIG. 1), and the load is set on the elastic material 1.

At this time, as the maximum distance position M1 of the cam 18 is positioned at the lowest point, the load set to the elastic material 1 becomes a maximum load at the time of deformation of the elastic material 1.

Incidentally, the load of the elastic material 1 can be measured with the load cell 26 of the first pusher 3.

Next, in the deforming step S12 in the present embodiment, by rotating the output shaft 14 (shown in FIG. 3) of the electric motor 11, the elastic material 1 is deformed (step S122).

In the step S122, as shown in FIGS. 4(a) and 4(b), by the rotation of the output shaft 14 of the electric motor 11, the base portion 16 of the conversion device 12 is linearly reciprocated.

In the step S122, by the linear reciprocating motion of the base portion 16 of the conversion device 12, the elastic material 1 is linearly reciprocated while being pressed onto the contacted surface 23.

Thereby, compression deformation of the elastic material 1 toward the contacted surface 23, and, relaxation of the compressive deformation are performed alternately.

Therefore, in the deformation step S12, based on the rotation of the electric motor 11, the elastic material 1 can be deformed in the predetermined cycles.

Next, in the projection image obtaining step S1 in the present embodiment, the capture signal St (shown in FIG. 1) is output at a predetermined specific time point in one cycle (the signal output step S13).

In the signal output step S13, the linear position detecting device 4 and the pulse generator 5 are used.

In the present embodiment, as shown in FIGS. 1, 3 and 4(a), in the state where the maximum distance position M1 of the cam 18 is positioned at the lowest point of the cam 18, the protrusion 32 is disposed in the space 38 of the frame 33. Therefore, the protrusion 32 is detected when the maximum distance position M1 of the cam 18 is positioned at the lowest point of the cam 18, and the detection signal Sg is output. When the detection signal Sg is input to the pulse generator 5, the pulse signal Sp (capture signal St) is output. Thus, in the signal output step S13, there is performed the step of detecting the specific position in the linear reciprocating motion of the elastic material 1, and outputting the capture signal St.

In the present embodiment, when the maximum distance position M1 of the cam 18 is positioned at the lowest point of the cam 18, the base portion 16 and the holder 13 of the conversion device 12 are pushed down mostly, and the compressive deformation of the elastic material 1 becomes maximized. Accordingly, in the signal output step S13 in the present embodiment, the capture signal St (pulse signal Sp) is output at the position (time point) at which the compressive deformation of the elastic material 1 becomes maximized, of the one cycle of the linear reciprocating motion of the elastic material 1. The time point when the capture signal St is output (i.e., the specific position in the linear reciprocating motion of the elastic material 1) can be set as appropriate by changing the position of the protrusion 32 with respect to the circumferential direction of the output shaft 14, or, the position of the cam 18.

Next, in the projection image obtaining step S1 in the present embodiment, based on the capture signal St, the projection image of the elastic material 1 is captured (capturing step S14).

As shown in FIG. 1, in the capturing step S14, at the time point when the capture signal St (pulse signal Sp) is input to the shutter trigger (not shown) of the x-ray camera 7, and the x-ray from the x-ray tube 47 is irradiated.

Thereby, in the capturing step S14, the projection image of the elastic material 1 is captured at the specific position in the linear reciprocating motion of the elastic material 1 (in the present embodiment, the position in the linear reciprocating motion of the elastic material 1 at which the compressive deformation of the elastic material 1 becomes maximum).

In the capturing step S14 in the present embodiment, captured is the projection image including at least a part of the contact portion between the elastic material 1 and the contacted surface 23 onto which the elastic material 1 is pressed.

The projection image of the elastic material 1 is stored in a computer (not shown) connected to the x-ray camera 7.

Next, in the projection image obtaining step S1 in the present embodiment, it is judged whether the capturing of the elastic material 1 is completed at a plurality of predetermined capture positions P (shown in FIG. 5) (step S15). In the step S15, if the capturing of the elastic material 1 is judged as being completed ("Y" in the step S15), then the subsequent three-dimensional image constructing step S2 is performed.

On the other hand, if the capturing of the elastic material 1 is judged as being not yet completed ("N" in the step S15), then the x-ray camera 7 is positioned at the next capture position P, and the deforming step S12—the step S15 are performed again.

Thereby, in the projection image obtaining step S1, the deforming step S12, the signal output step S13 and the capturing step S14 are performed at each of the capture positions P. Therefore, in the projection image obtaining step S1, even if the elastic material 1 is periodically deformed, at each of the capture positions P, it is always possible to capture the projection image in the specific state of the deformation (deformation at the specific moment).

In order that the projection image of the specific deformed state can be reliably captured at a plurality of the capture positions P (shown in FIG. 5), it is desirable that the decay time of the phosphor (not shown) of the detector 48 is set to 100 ms or less.

Incidentally, if the decay time of the phosphor becomes more than 100 ms, a residual image of the previously captured projection image is liable to occur. Thus, there is a possibility that the capturing of the projection image at a plurality of the capture positions P becomes difficult.

From this point of view, the decay time of the phosphor is preferably nor more than 50 ms, more preferably not more than 10 ms. If the decay time of the phosphor is too short, the efficiency of the conversion of photoelectrons to visible light may be reduced. From this point of view, the decay time of the phosphor is preferably not less than 0.1 ms.

From the same point of view, the intensity of the x-ray (photons/s/mrad$^2$/mm$^2$/0.1% bw) is preferably not less than $10^{10}$, more preferably not less than $10^{12}$.

Next, in the observing method in the present embodiment, from the projection images of the elastic material 1, a three-dimensional image of the elastic material 1 is constructed (three-dimensional image constructing step S2).

Figure 9:
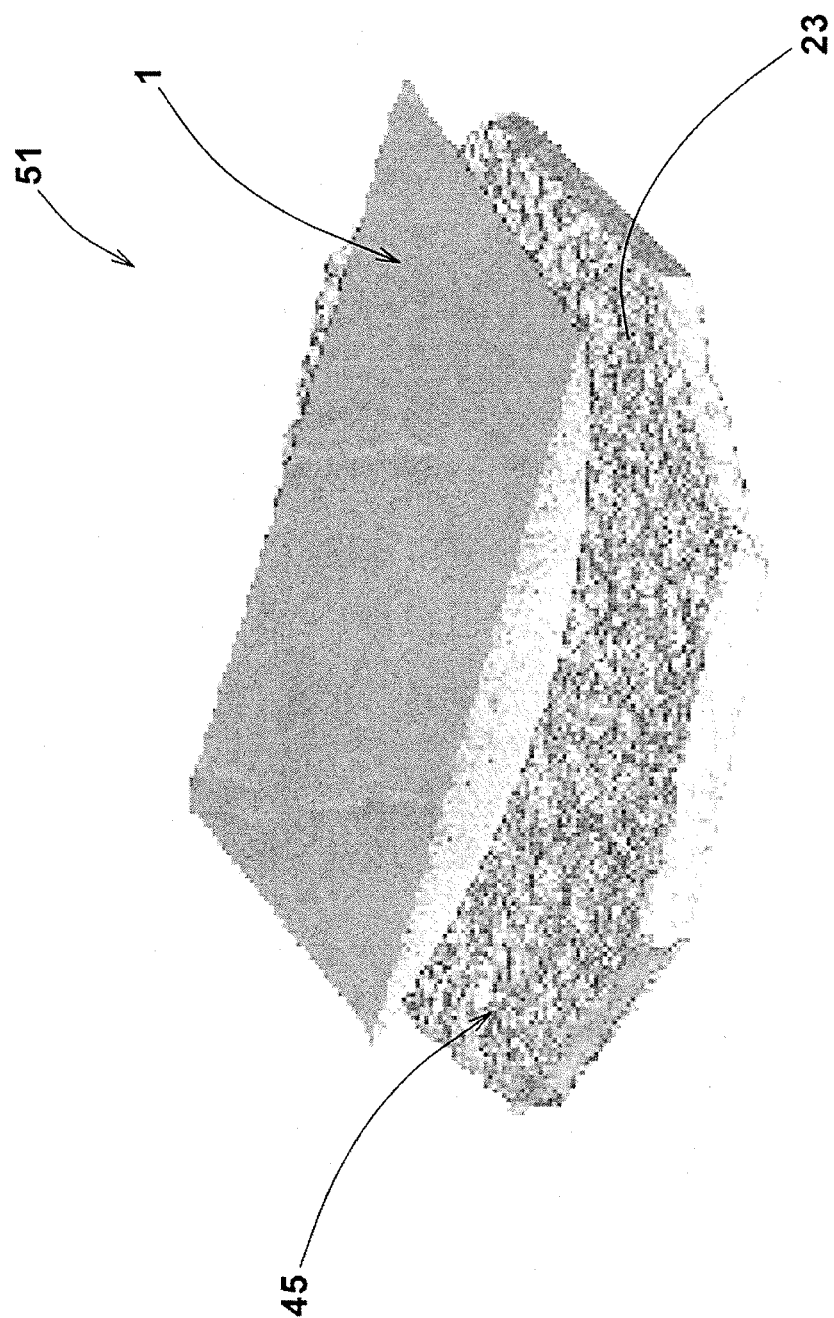
FIG. 9 A three-dimensional image of the elastic material and the contacted surface.

FIG. 9 is a three-dimensional image of the elastic material 1 and the contacted surface 23.

Figure 10:
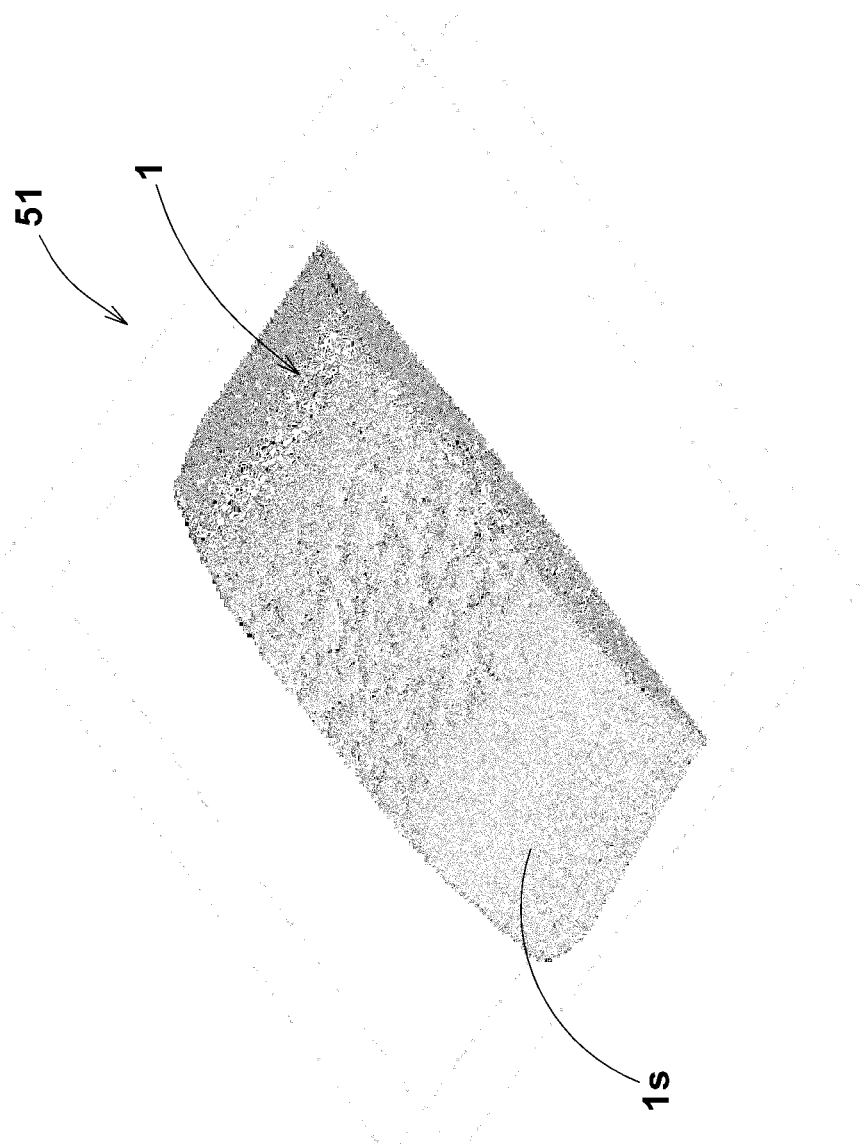
FIG. 10 A three-dimensional image of the outer peripheral surface of the elastic material viewed from the under side.

FIG. 10 is a three-dimensional image of the outer peripheral surface 1s of the elastic material 1 viewed from the under side.

In the three-dimensional image constructing step S2 in the present embodiment, for example, according to the Convolution Back Projection method, by reversely projecting the projection images of the elastic material 1 captured at a plurality of the capture positions P (shown in FIG. 5) as is conventionally done, the three-dimensional image 51 of the elastic material 1 can be constructed.

A plurality of the projection images of the elastic material 1 are captured, in the projection image obtaining step S1, at the specific position in the linear reciprocating motion of the elastic material 1, (in the present embodiment, at the position in the linear reciprocating motion of the elastic material 1 at which the compressive deformation of the elastic material 1 becomes maximum).

Therefore, in the three-dimensional image constructing step S2, a three-dimensional image 51 under the specific state of deformation (deformation moment) can be obtained.

Next, in the observing method in the present embodiment, the three-dimensional image 51 of the elastic material 1 is observed (step S3).

In the present embodiment, by observing the three-dimensional image 51, it is possible to directly observe the specific deformed state (deformation moment) of the actual elastic material 1 which is being deformed periodically.

Therefore, in the observing method in the present embodiment, performance of the elastic material 1 can be assessed accurately. Further, based on the deformed state of the elastic material 1, it is possible, for example, to create a rubber model for use in a simulation based on the finite element method, and define boundary conditions.

Thus, the observing method in the present embodiment is useful for improving the simulation accuracy.

It is desirable that the elastic material 1 contains marker particles.

Figure 11:
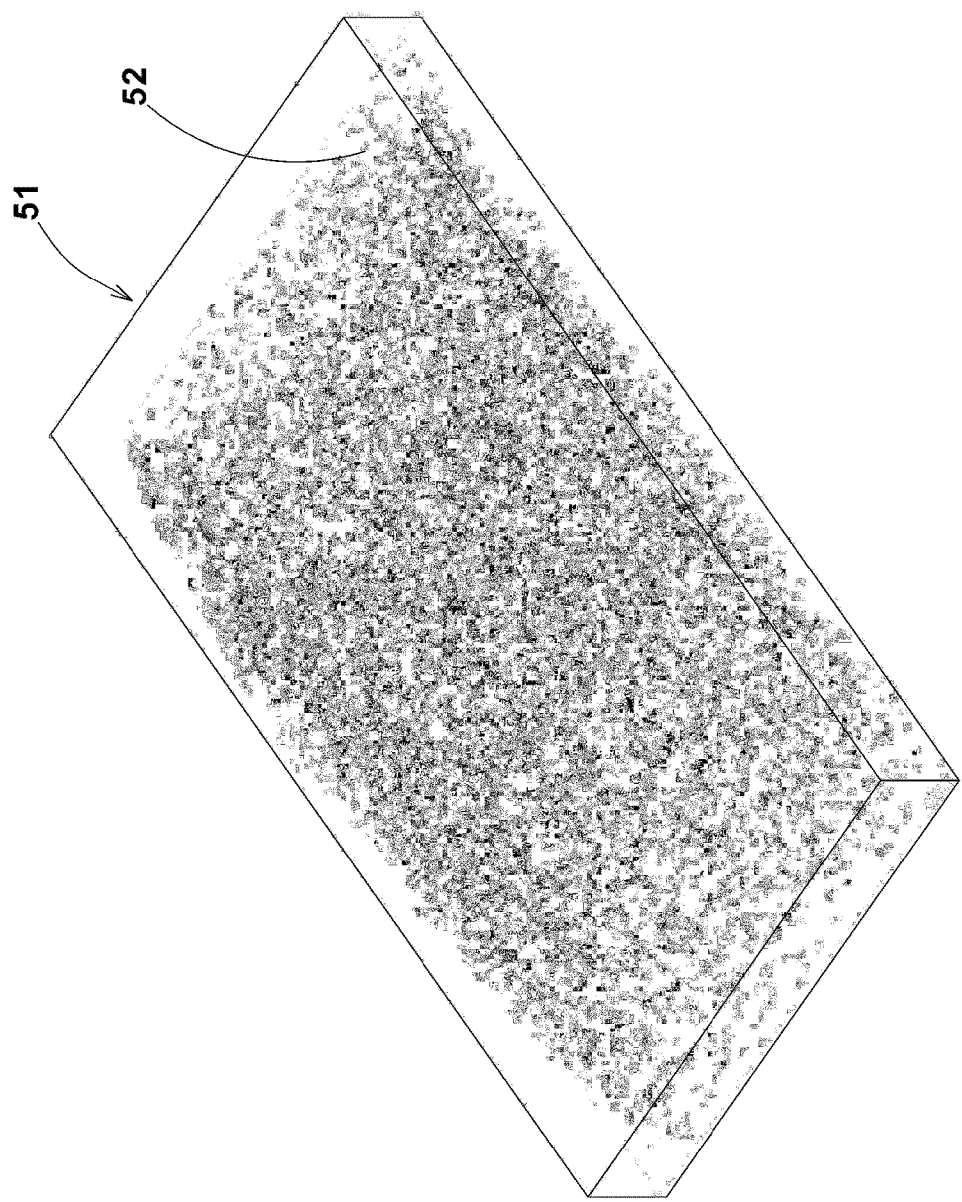
FIG. 11 A three-dimensional image of the elastic material containing the marker particles.

FIG. 11 is a three-dimensional image 51 of the elastic material 1 containing marker particles 52.

As the marker particles 52 in the present embodiment, for example, alumina particles having a diameter of about 40 micrometers are used.

Such marker particles 52 are displayed emphatically in the three-dimensional image 51, and the deformed shape of the elastic material 1 can be accurately measured.

Further, the strain distribution of the elastic material 1 can be obtained from the positional information on the marker particles 52 based on a digital image correlation method. The marker particles 52 are not limited to alumina particles. Other marker particles 52 can be employed as appropriate as far as the density is more than the rubber (e.g., barium sulfate, etc.), It is desirable that the content of the marker particles 52 is 1 to 100 parts by mass.

Incidentally, if the content of the marker particles 52 is less than 1 parts by mass, there is possibility that a specific deformed state (deformation moment) of the elastic material 1 can not be accurately observed.

If the content of the marker particles 52 is more than 100 parts by mass, as physical properties of the elastic material 1 are changed significantly, there is possibility that the performance of the elastic material 1 can not be accurately evaluated.

From this point of view, the content of the marker particles 52 is preferably not less than 5 parts by mass, more preferably not less than 10 parts by mass.

The content of the marker particles 52 is preferably not more than 70 parts by mass, more preferably not more than 50 parts by mass.

In the projection image capture apparatus 2 in the present embodiment, the deformation means 2A is constructed by the first pusher 3 to linearly reciprocate the elastic material 1. But it is not limited thereto. For example, the deforming means 2A may be constructed by a second pusher which rotates the outer peripheral surface is of the elastic material 1 while pressing it onto the contacted surface 23.

Figure 12:
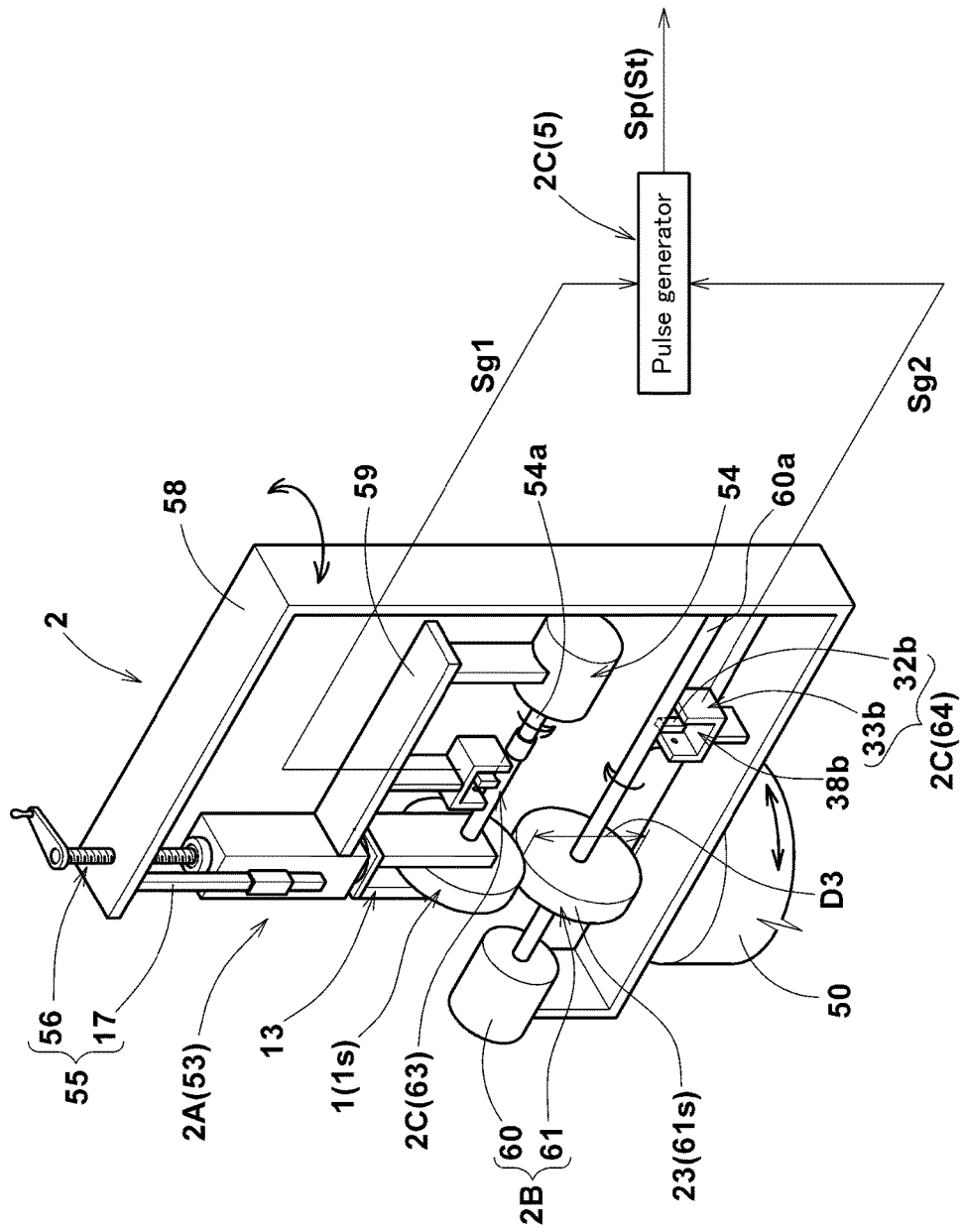
FIG. 12 A perspective view of an apparatus for capturing a projection image of the elastic material according to another embodiment of the present invention.

FIG. 12 is a perspective view of the projection image capture apparatus in the present embodiment.

Figure 13:
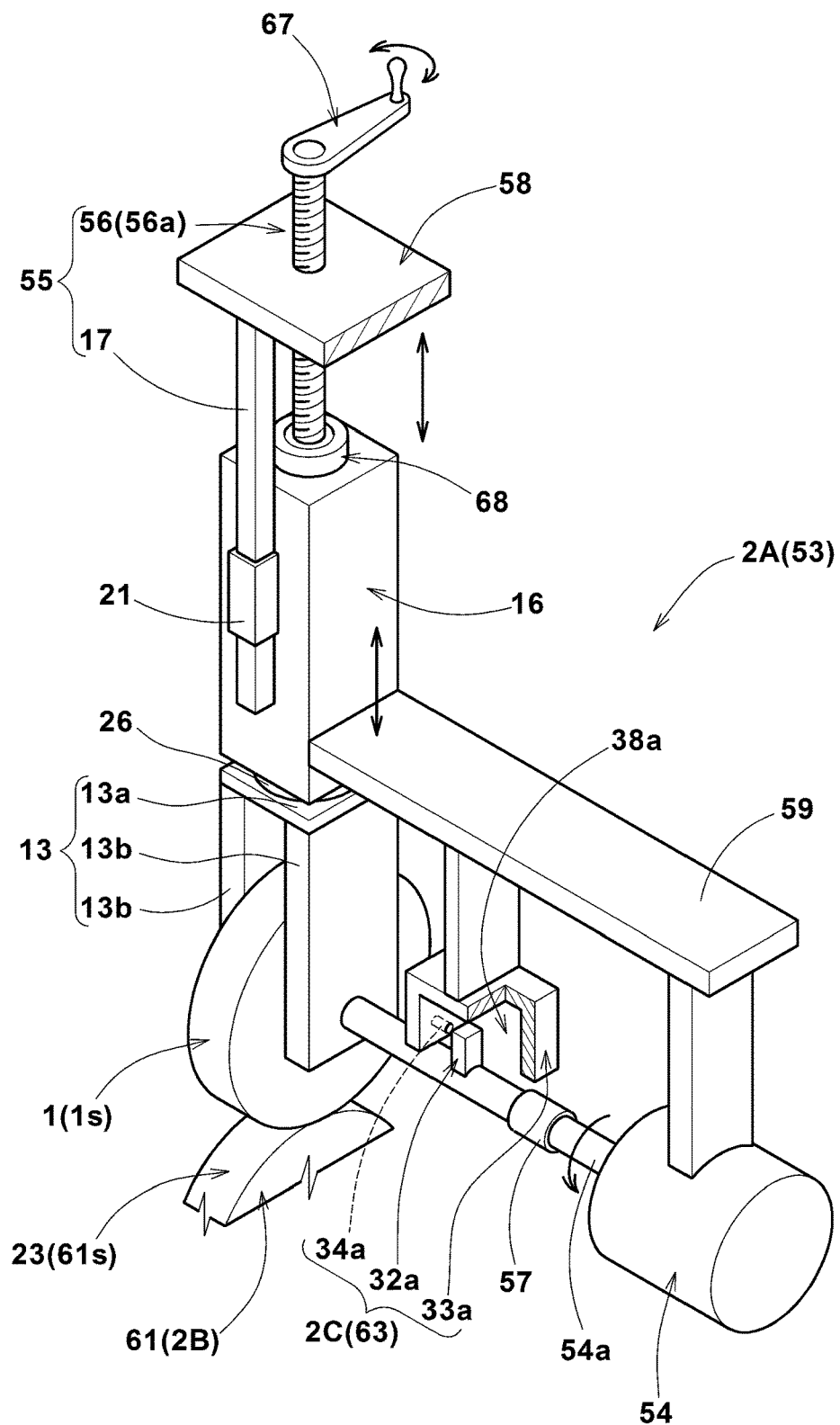
FIG. 13 An enlarged perspective view showing a second pusher.

FIG. 13 is an enlarged perspective view of the second pusher 53.

Incidentally, there are cases where the same configuration as in the former embodiment and a step of carrying out the same process as in the former embodiment are denoted by the same reference numerals and the descriptions are omitted in the present embodiment.

the projection image capture apparatus 2 in the present embodiment includes a deforming means 2A composed of the second pusher 53, the contact base 2B, the capture signal outputting means 2C, and the capturing means 2D (not shown).

The capturing means 2D is of the same structure as the capturing means 2D in the former embodiment (shown in FIG. 1).

As shown in FIG. 13, the second pressing tool 53 is provided with a holder 13 for holding the elastic material 1, a first rotating means 54 for rotating the elastic material 1, and an adjuster 55 for changing the distance between the holder 13 and the contacted surface 23.

The holder 13 is of the same structure as the holder 13 in the former embodiment (shown in FIG. 3).

Further, the second pusher 53 is provided with a base portion 16 extending in the up-down direction similarly to the first pusher 3 shown in FIG. 3.

As to the first rotating means 54, for example, an AC or DC electric motor is employed.

The first rotating means 54 in the present embodiment is disposed above the first rotating means 54, and is supported by a frame 59 fixed to the base portion 16.

Further, the first rotating means 54 is provided with the first output shaft 54a rotatable about a horizontal axis.

The other end of the first output shaft 54a (on the opposite side to the first rotating means 54 in the axial direction of the first output shaft 54a) is supported by a pair of the vertical plates 13b, 13b of the holder 13, rotatably around a horizontal axis.

Further, the first output shaft 54a is fixed to the hole 1o of the elastic material 1 (shown in FIG. 2).

Thus, by rotating the first output shaft 54a, the elastic material 1 can be rotated about a horizontal axis.

Further, the first output shaft 54a, may be provided with a torque meter 57 for measuring the torque of the first output shaft 54a.

The adjuster 55 includes a rail portion 17, and a moving means 56 for moving the base portion 16 in the up-down direction.

The rail portion 17 extends in the up-down direction on one side of the base portion 16 similarly to the rail portion 17 in the former embodiment (shown in FIG. 2).

The upper end of the rail portion 17 is fixed to the support frame 58 fixed to the rotating means 50 (shown in FIG. 12). The rail portion 17 is engaged with the slide mechanism 21 of the base portion 16.

The base portion 16 can be guided in the up-down direction by such rail portion 17.

The moving means 56 includes a threaded shaft 56a extending in the up-down direction.

The threaded shaft 56a is screwed to the support frame 58. The lower end of the threaded shaft 56a is attached to the upper end of the base portion 16 through a rotary joint 68 which is rotatable about a vertical axis.

Further, the upper end of the threaded shaft 56a is provided with a handle portion 67 for rotating the threaded shaft 56a about the vertical axis In the moving means 56, by rotating the threaded shaft 56a about the vertical axis, the threaded shaft 56a is moved in the up-down direction relative to the support frame 58. By the movement of the threaded shaft 56a in the up-down direction, the base portion 16 is moved in the up-down direction. Further, by the vertical movement of the base portion 16, the holder 13 fixed to the base portion 16 is moved in the up-down direction.

By such moving means 56, the distance between the holder 13 and the contacted surface 23 (the distance between the contacted surface 23 and the elastic material 1 held by the holder 13) can be varied.

Further, since the frame 59 is moved in the up-down direction with the vertical movement of the base portion 16, the first rotary unit 54 fixed to the frame 59 and the undermentioned first frame 33a of the first rotational position detecting device 63 are moved in the up-down direction together with the elastic material 1.

As shown in FIG. 12, the contact base 2B in the present embodiment is configured to include a drum 61 and a second rotating means 60.

The drum 61 is formed in a cylindrical shape rotatable about a horizontal axis.

The contacted surface 23 onto which the outer peripheral surface 1s of the elastic material 1 is pressed, is formed in the outer peripheral surface 61s of the drum 61.

It is desirable that, in the contacted surface 23, for example, a plurality of grooves 62 (shown in FIG. 15) extending in the drum's axial direction are arranged in the drum's circumferential direction at intervals.

Further, the contacted surface 23 may be provided with a road surface simulating irregularities of the asphalt pavement.

As to the second rotating means 60, for example, an AC or DC electric motor is used.

The second rotating means 60 is fixed to the support frame 58. Further, the second rotating means 60 is provided with a second output shaft 60a rotatable about a horizontal axis.

The opposite side end of the second output shaft 60a (the opposite side of the second rotating means 60 in the axial direction of the second output shaft 60a) is supported by the support frame 58 rotatably about a horizontal axis.

Further, the second output shaft 60a is fixed to the axis of the drum 61. Thus, by rotating the second output shaft 60a, the drum 61 can be rotated about a horizontal axis. Accordingly, the second rotating means 60 can move the contacted surface 23 of the drum 61 in the circumferential direction.

In the second rotating means 60, the second output shaft 60a is rotated in the reverse direction of the first output shaft 54a of the first rotating means 54.

Thus, at the contacted surface 23, the drum 61 can rotate the elastic material 1.

In the present embodiment, the slip angle between the moving direction of the contacted surface 23 of the drum 61 and the moving direction of the outer peripheral surface is of the elastic material 1 is set to zero.

Thereby, on the elastic material 1, deformation of a tread rubber of a tire during straight traveling can be artificially reproduced.

The outer diameter D3 of the drum 61 can be set arbitrarily. For example, it is desirable that the outer diameter D3 of the drum 61 is set to be an integral multiple of the outer diameter D1 (shown in FIG. 2) of the elastic material 1. Accordingly, when the slip ratio of the elastic material 1 and the contacted surface 23 is zero, it is possible to always contact a specific position of the elastic material 1 with a specific position of the drum 61.

In the present embodiment, the outer diameter D3 of the drum 61 is set to be the same as the outer diameter D1 of the elastic material 1.

The rotational speed of the first rotating means 54 and the rotational speed of the second rotating means 60 may be set arbitrarily. For example, if the outer diameter D3 of the drum 61 is more than the outer diameter D1 (shown in FIG. 2) of the elastic material 1, the rotational speed of the first rotating means 54 may be set to be higher than the rotational speed of the second rotating means 60 so that the slip ratio of the elastic material 1 and the drum 61 is zero.

Further, by respectively setting the rotational speed of the first rotating means 54 and the rotational speed of the second rotating means 60, the deformation of a tread rubber of a tire at the time of acceleration or deceleration is artificially reproduced.

In the contact base 2B, for example, a flat-belt (not shown) may be used instead of the drum 61 in the present embodiment. According to such flat belt, the shape of the contact portion between the elastic material 1 and the contacted surface 23 becomes flat, and a tire during running can be more accurately reproduced.

In the present embodiment, there is provided the rotating means 50 for rotating the second pusher 53 and the contact base 2B around the vertical axis through the support frame 58. Such rotating means 50 can move the elastic material 1 and the contacted surface 23, relatively to the capturing means 2D (x-ray camera 7) shown in FIGS. 1 and 5.

As shown in FIGS. 12 and 13, in the capture signal outputting means 2C in the present embodiment, the first rotational position detecting device 63, the second rotational position detecting device 64 and the pulse generator 5 are included.

The first rotational position detecting device 63 is for the purpose of detecting a specific position in the rotation of the elastic material 1.

As shown in FIG. 13, similarly to the linear position detecting device 4 in the former embodiment, the first rotational position detecting device 63 in the present embodiment includes
a first protrusion 32a protruding radially outward from the first output shaft 54a,
the first frame 33a disposed above the first output shaft 54a,
a first sensor 34a for detecting the first protrusion 32a, and
the output unit (not shown) for outputting a detection signal Sg1 (shown in FIG. 12).

In such first rotational position detecting device 63, the first protrusion 32a passing through the space 38a of the first frame 33a can be detected by the first sensor 34a. Further, when the passage of the first protrusion 32a is detected, as shown in FIG. 12, the detection signal Sg1 is output from the output unit (not shown) towards the pulse generator 5.

By the rotation of the first output shaft 54a, the outer peripheral surface is of the elastic material 1 and the first protrusion 32a are rotated at the same cycle.

Accordingly, in the first rotational position detecting device 63, by the detection of the first projecting portion 32a, the specific position of the outer peripheral surface 1s of the elastic material 1 can be detected.

As shown in FIG. 12, the second rotational position detecting device 64 is for the purpose of detecting a specific position in the movement of the contacted surface 23.

The second rotational position detecting device 64 includes a second protrusion 32b protruding radially outwardly from the second output shaft 60a, a second frame 33b disposed below the second output shaft 60a, a second sensor (not shown) for detecting the second protrusion 32b, and an output unit (not shown) for outputting a detection signal Sg 2.

In such second rotational position detecting device 64, the second protrusion 32b passing through the space 38b of the second frame 33b can be detected by the second sensor (not shown).

Further, when the passage of the second protrusion 32*b* is detected, the detection signal Sg2 is output from the output unit (not shown) toward the pulse generator 5.

By the rotation of the second output shaft 60*a*, the outer peripheral surface 61*s* of the drum 61 and the second protrusion 32*b* are rotated at the same cycle.

Therefore, in the second rotational position detecting device 64, by the detection of the second protrusion 32*b*, the specific position of the outer peripheral surface 61*s* of the drum 61 can be detected.

In the pulse generator 5, the pulse signal Sp is output by simultaneously inputting the detection signal Sg1 of the first rotational position detecting device 63 and the detection signal Sg2 of the second rotational position detecting device 64. As described above, the detection signal Sg1 is output by the detection of the specific position on the outer peripheral surface is of the elastic material 1.

Further, the detection signal Sg2 is output by the detection of the specific position on the outer peripheral surface of the drum 61.

Thus, in the present embodiment, the pulse signal Sp (capture signal St) can be output at the time point (specific time point in one cycle) when the specific position of the outer peripheral surface is of the elastic material 1 contacts with the specific position of the outer peripheral surface 61*s* of the drum 61.

Incidentally, in the initial state of the elastic material 1 contacted with the drum 61, it is preferable that the first protrusion 32*a* is disposed in the space 38*a* of the first frame 33*a* (shown in FIG. 13), and the second protrusion 32*b* is disposed in the space 38*b* of the second frame 33*b*.

Accordingly, the pulse signal Sp (capture signal St) can be output at a time point when the outer peripheral surface 1*s* of the elastic material 1 contacts with the outer peripheral surface 61*s* of the drum 61 at the contacting position in the initial state.

Next, the observing method using the projection image capture apparatus 2 in the present embodiment is described. In the projection image obtaining step S1 in the present embodiment, a projection image including at least part of the contact portion is captured from a direction perpendicular to the axis of the elastic material 1 (the vertical axis L3 in the present embodiment) at a plurality of capture positions P around the axis similarly to the observing method in the former embodiment shown in FIGS. 1 and 5.

Incidentally, in the observing method in the present embodiment, the elastic material 1 whose outer peripheral surface is circular is used.

In the projection image obtaining step S1 in the present embodiment, first, the x-ray camera 7 as the capturing means 2D is positioned at the capture start position Ps shown in FIG. 5 (step S11).

In the step S1 in the present embodiment, the second pusher 53 and the contact base 2B are rotated around the vertical axis by the rotating means 50, and the x-ray camera 7 is positioned at to the capture start position Ps.

Next, in the projection image obtaining step S1 in the present embodiment, the elastic material 1 is deformed in the predetermined cycles (deforming step S12).

In the step S12 in the present embodiment, the second pusher 53 and the contact base 2B shown in FIGS. 12 and 13 are used.

Figure 14:
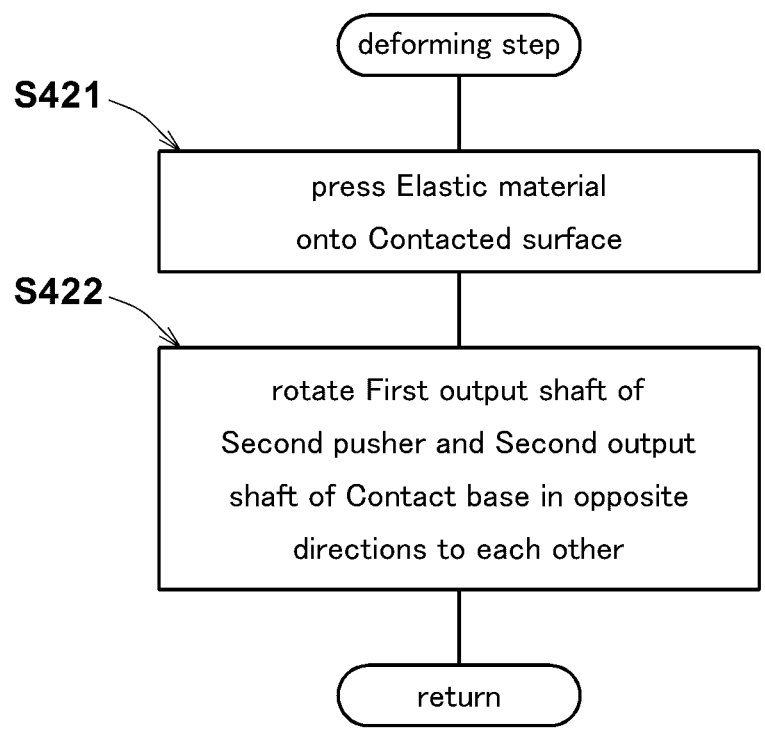
FIG. 14 A flowchart illustrating an example of the processing procedure of the deforming step of another embodiment of the present invention.

FIG. 14 is a flowchart illustrating an example of the processing procedure of the deforming step S12 in the present embodiment.

In the deforming step S12 in the present embodiment, first, the elastic material 1 is pressed onto the contacted surface 23 (step S421).

In the step S421, as shown in FIGS. 12 and 13, the first protrusion 32*a* is disposed in the space 38*a* of the first frame 33*a*.

Further, the second projection portion 32*b* is disposed in the space 38*b* of the second frame 33*b*.

Then, by the moving means 56 of the adjuster 55, the base portion 16 of the second pusher 53 is moved up and down. Thereby, the load is set on the elastic material 1 contacting with the drum 61.

The load applied to the elastic material 1 may be defined to be equal to the load applied to the actual tire (ground contact pressure) for example.

Next, in the deforming step S12 in the present embodiment, the first output shaft 54*a* of the second pusher 53 and the second output shaft 60*a* of the contact base 2B are rotated in the opposite directions to each other (step S422).

Thus, in the step S422, the outer peripheral surface is of the elastic material 1 can be rotated (deformed) while being pressed onto the contacted surface 23.

Therefore, in the deforming step S42, based on the rotation of the first rotating means 54 and the second rotating means 60, the elastic material 1 can be deformed in predetermined cycles.

Next, in the projection image obtaining step S1 in the present embodiment, the capture signal St is output at a predetermined specific time point in the one cycle (the signal output step S13).

The signal output step S13 in the present embodiment uses the capture signal outputting means 2C including the first rotational position detecting device 63, the second rotational position detecting device 64, and the pulse generator 5.

As described above, in the first rotational position detecting device 63 and the second rotational position detecting device 64, when the first protrusion 32*a* and second protrusion 32*b* are detected, the detection signals Sg1, Sg2 are output toward the pulse generator 5.

Further, in the pulse generator 5 in the present embodiment, when the detection signal Sg1 of the first rotational position detecting device 63 and the detection signal Sg2 of the second rotational position detecting device 64 are input at the same time, the pulse signal Sp is output.

Accordingly, in the signal output step S13 in the present embodiment, the pulse signal Sp (capture signal St) can be output at the time point (specific time point in one cycle) when the specific position of the outer peripheral surface is of the elastic material 1 comes into contact with the specific position of the outer peripheral surface 61*s* of the drum 61. The time point when the capture signal St is output can be appropriately adjusted by changing the fixed positions of the first protrusion 32*a* and the second protrusion 32*b*.

Next, in the projection image obtaining step S1 in the present embodiment, based on the capture signal St, the projection image of the elastic material 1 is captured (capture step S14).

In the capturing step S14, the projection image of the elastic material 1 is captured at the specific position of the elastic material 1 during rotating (in the present embodiment, the time point when the specific position of the outer peripheral surface is of the elastic material 1 comes into contact with the specific position of the outer peripheral surface 61*s* of the drum 61).

In the capturing step S14 in the present embodiment, there is captured the projection image including at least part of the contact portion between the elastic material 1 and the contacted surface 23 onto which the elastic material 1 is pressed.

The projection image of the elastic material 1 is stored in a computer (not shown) connected to the x-ray camera 7 shown in FIG. 1.

Next, in the projection image obtaining step S1 in the present embodiment, it is judged whether the capturing of the elastic material 1 is completed at a plurality of the predetermined capture positions P (shown in FIG. 5) (step S15). In this step S15, if the capturing of the elastic material 1 is judged as being completed ("Y" in the step S15), then the subsequent three-dimensional image constructing step S2 is performed.

On the other hand, if the capturing of the elastic material 1 is judged as being not yet completed ("N" in the step S15), the x-ray camera 7 is positioned at the next capture position P (step S16), and the deforming step S12—the step S15 are performed again.

Thus, in the projection image obtaining step S1 in the present embodiment, the deforming step S12, the signal output step S13, and the capturing step S14, are performed at each of the capture positions P.

Accordingly, in the projection image obtaining step S1 in the present embodiment, it is always possible to capture the projection image of the specific state of deformation (deformation moment) at each of the capture positions P.

Next, in the observing method of the embodiment, from the projection images of the elastic material 1, a three-dimensional image of the elastic material 1 is constructed (three-dimensional image constructing step S2).

Figure 15:
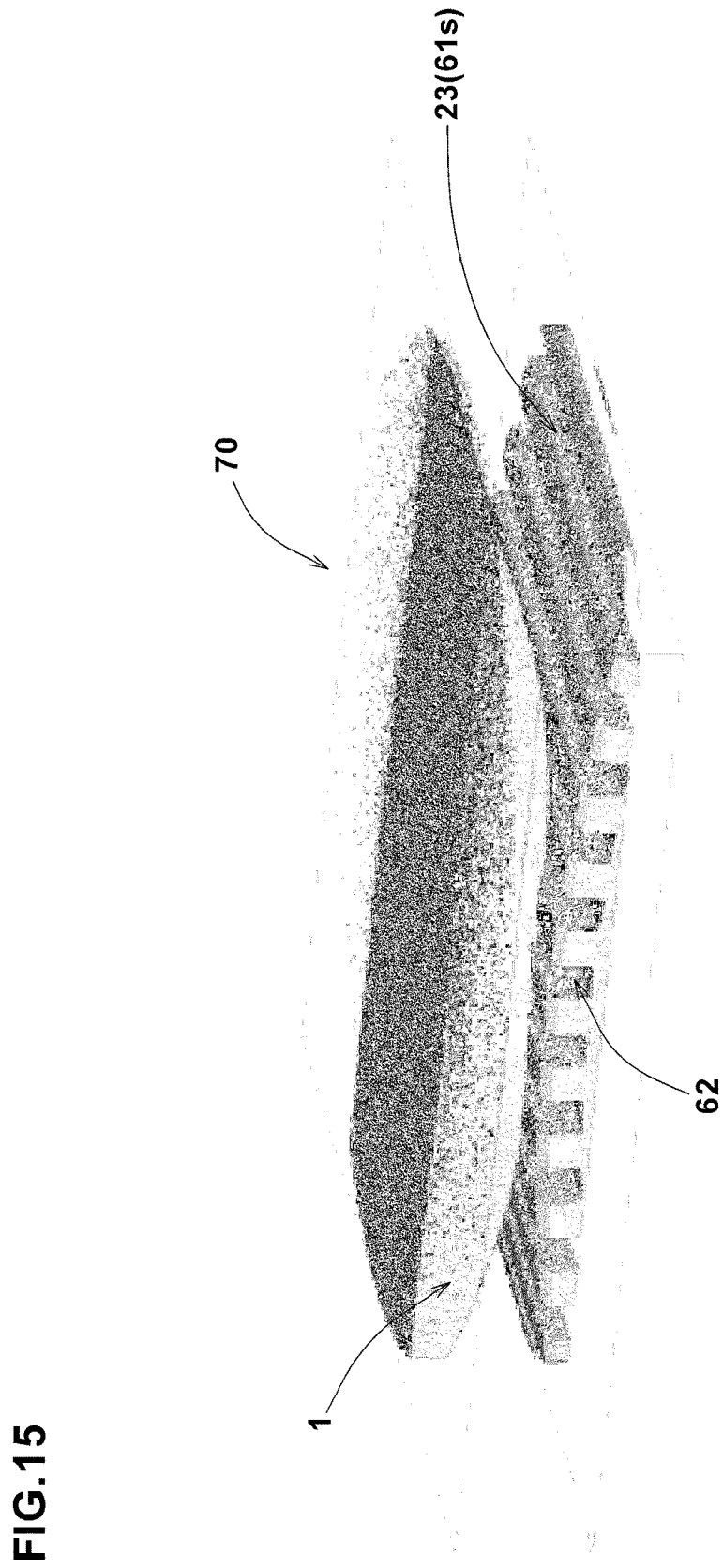
FIG. 15 A three-dimensional image of the elastic material and the drum.

FIG. 15 is a three-dimensional image 70 of the elastic material 1 and the drum 61.

In the three-dimensional image constructing step S2, the three-dimensional image 70 of the elastic material 1 can be constructed by the same method as in the former embodiment. Accordingly, in the three-dimensional image constructing step S2, the three-dimensional image 70 under a specific deformed state (in the present embodiment, the three-dimensional image including concavity and convexity existing at specific positions on the outer peripheral surface 61s of the drum 61 (the contacted surface 23), and the elastic material deformed by the concavity and convexity) can be obtained.

Next, in the observing method in the present embodiment, a three-dimensional image 70 of the elastic material 1 is observed (step S3).

In the present embodiment, by observing the three-dimensional image 70, a particular deformation (deformation moment) of the elastic material 1 which is rolling on the contacted surface 23 can be directly observed.

Therefore, in the observing method in the present embodiment, performance of the elastic material 1 can be assessed accurately.

In the present embodiment too, it is preferable that the elastic material 1 contains marker particles 52 (shown in FIG. 11) as in the former embodiment, in order to emphatically capture the three-dimensional image 70.

Thus, it is possible to obtain the strain distribution of the elastic material 1 frictioning against the contacted surface 23.

In the projection image capture apparatus 2 in the present embodiment, the slip angle between the moving direction of the contacted surface 23 of the drum 61 and the moving direction of the outer peripheral surface is of the elastic material 1, is set to zero, but it is not limited thereto. For example, it may be possible to further include a slip angle setting means for setting a slip angle to the elastic material 1 rolling on the contacted surface 23.

Figure 16:
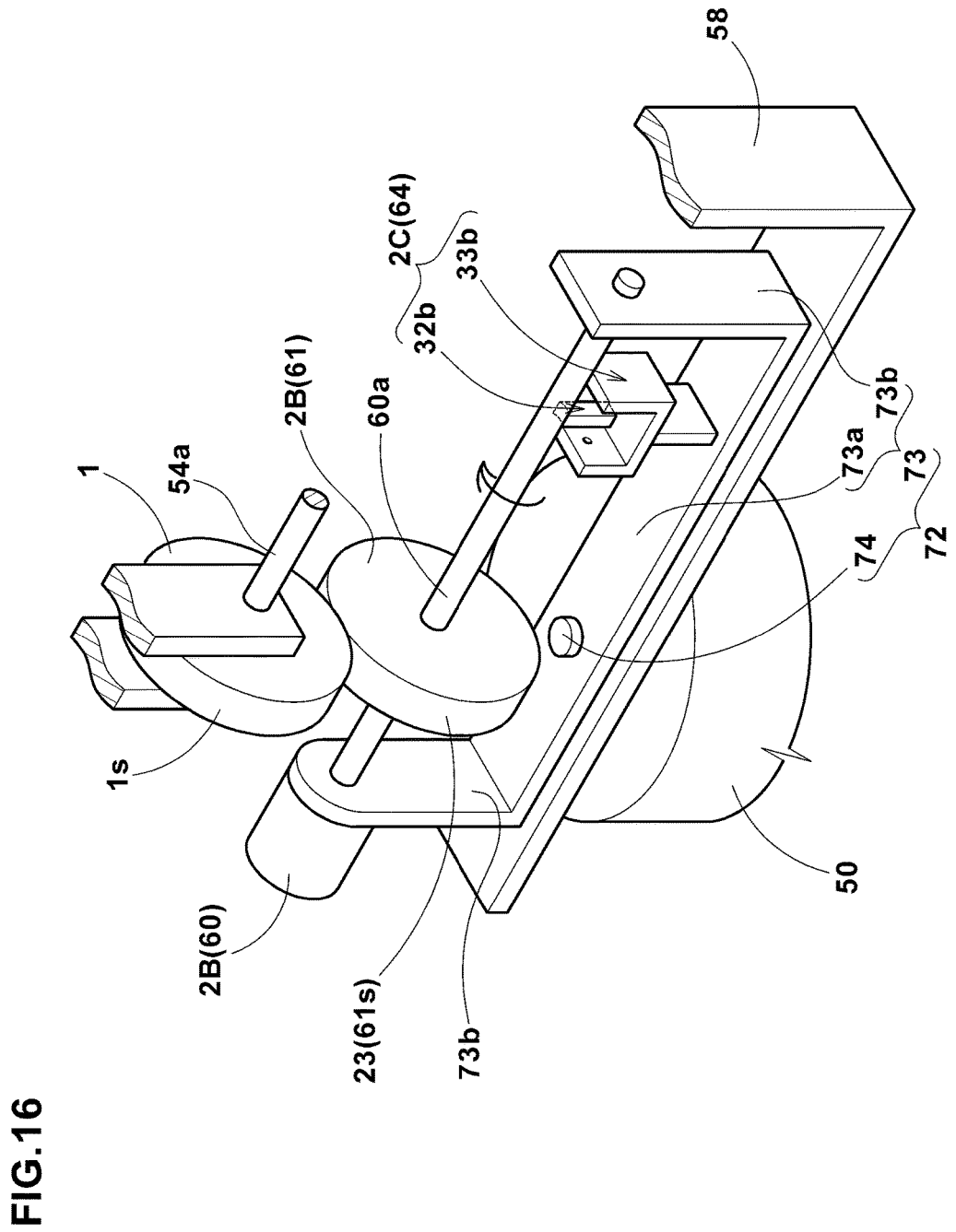
FIG. 16 A perspective view showing the slip angle setting means.

FIG. 16 is a perspective view showing the slip angle setting means.

Figure 17:
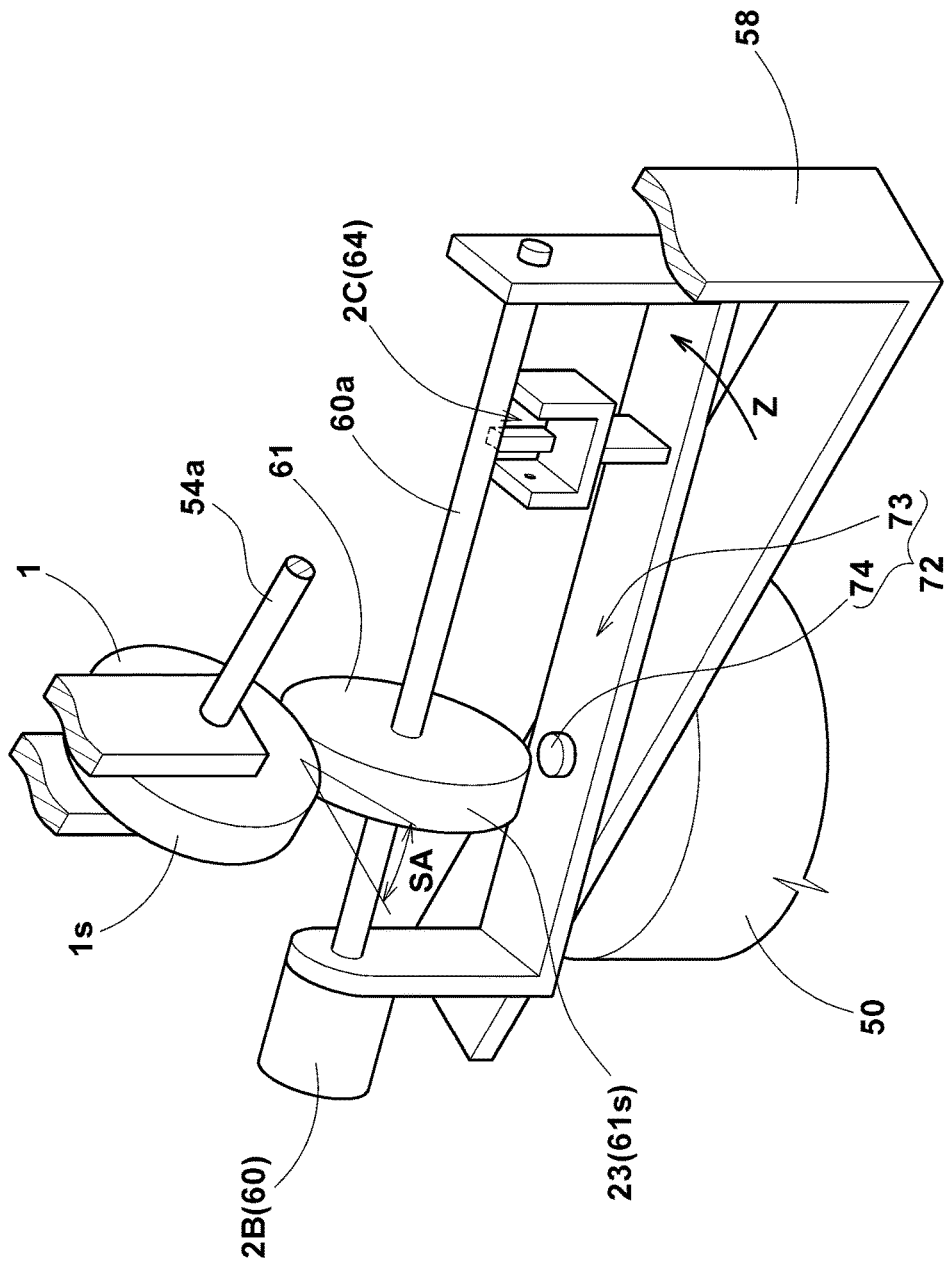
FIG. 17 A perspective view showing a state where the slip angle is set for the elastic material by the slip angle setting means shown in FIG. 16.

FIG. 17 is a perspective view showing a state where a slip angle is set to the elastic material by the slip angle setting means of FIG. 16.

Incidentally, in the present embodiment, there are cases where a configuration same as in the former embodiment, and a step of carrying out the same process as in the former embodiment are denoted by the same reference numerals, and their descriptions are omitted.

The slip angle setting means 72 in the present embodiment is, for example, provided with a support base 73 and a supporting shaft 74.

The support base 73 includes a horizontal plate 73a extending horizontally and a pair of vertical plates 73b, 73b extending upwardly from both ends of the horizontal plate 73a, and is formed in a substantially u-shaped in the front view. The second rotating means 60 is fixed to one of the vertical plates 73b.

Further, by a pair of the vertical plates 73b, 73b, the second output shaft 60a to which the drum 61 is fixed, is supported rotatably about a horizontal axis.

In such support base 73, the drum 61 can be rotated about the horizontal axis by the rotation of the second rotating means 60. Further, to the support base 73, the second frame 33b of the second rotational position detecting device 64, and the second sensor (not shown) are fixed.

Between the support frame 58 and the horizontal plate 73a, the supporting shaft 74 extends in the up-down direction.

In such a support shaft 74, the support base 73 can be supported rotatably around the vertical axis with respect to the support frame 58.

As shown in FIG. 17, in the present embodiment, the moving direction of the outer peripheral surface is of the elastic material 1 is fixed.

The support base 73 is rotated around the support shaft 74 in the arrow z direction with reference to the support frame 58. Thus, the drum 61 is provided with an attitude angle, and a relative slip angle SA is given between the elastic material 1 and the drum 61.

Incidentally, when the slip angle SA is set, in order to prevent the grounding surface of the elastic material 1 from being reduced, it is desirable that the width of the drum 61 is set to be greater than the width W1 (shown in FIG. 2) of the elastic material 1.

Next, the observing method using the projection image capture apparatus 2 in the present embodiment is described. The observing method in the present embodiment is the same as the processing procedure of the observing method in the former embodiment, except for the deforming step S12 in the projection image obtaining step S1.

Figure 18:
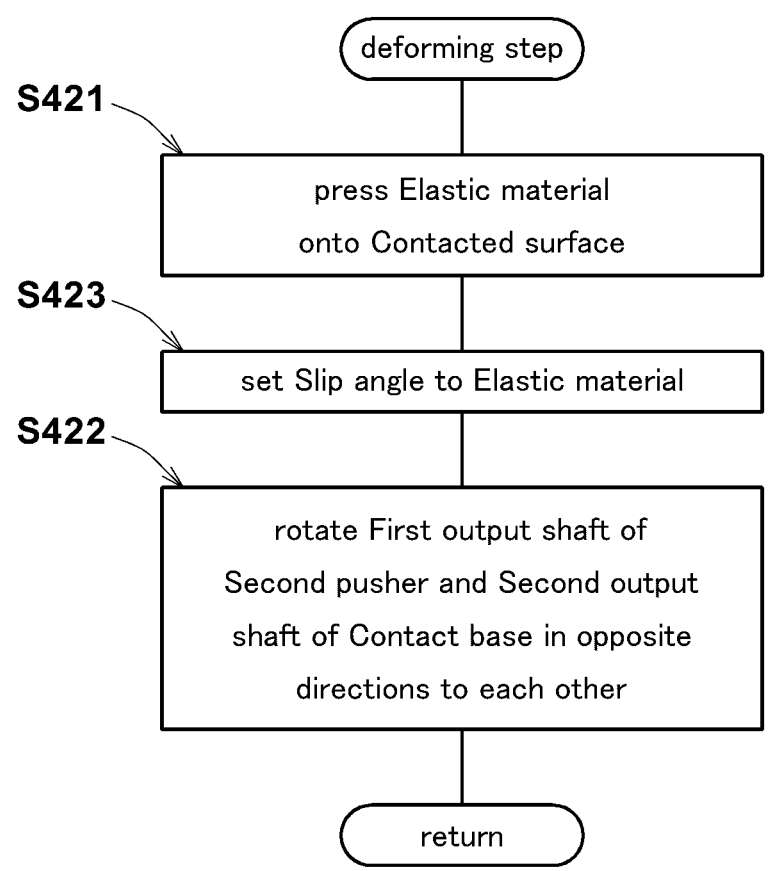
FIG. 18 A flowchart illustrating an example of the processing procedure of the deforming step of still another embodiment of the present invention.

FIG. 18 is a flowchart illustrating an example of the processing procedure of the deforming step S12 in the present embodiment.

In the deforming step S12 in the present embodiment, the second pusher 53 (shown in FIGS. 12 and 13), the contact base 2B, and the slip angle setting means 72 are used.

In the deforming step S12, first, as shown in FIG. 16, the elastic material 1 is pressed onto the contacted surface 23 (step S421).

The processing procedure of the step S421 is the same as the processing procedure of the step S421 of the former embodiment.

Next, in the deforming step S12 in the present embodiment, a slip angle SA (shown in FIG. 17) is set to the elastic material 1 (step S423).

As shown in FIGS. 16 and 17, in the step S423, with reference to the support frame 58, the support base 73 is rotated around the support shaft 74.

Accordingly, the slip angle SA is set to the elastic material 1. The slip angle SA may be set as appropriate.

In the present embodiment, the slip angle SA is determined to be equal to the slip angle imparted to the actual tire.

Next, in the deforming step S12 in the present embodiment, the first output shaft 54a of the second pusher 53 and the second output shaft 60a of the contact base 2B are rotated in the opposite directions to each other (step S422). In the step S422, in a state in which the slip angle SA has been set to the elastic material 1, the elastic material 1 can be rotated (deformed) while the outer peripheral surface is of the elastic material 1 is pressed onto the contacted surface 23. Therefore, in the deforming step S42, based on the rotation of the first rotating means 54 and the second rotating means 60, the elastic material 1 can be deformed in predetermined cycles.

Then, in the observing method in the present embodiment, in the same manner as the observing method in the former embodiment, at each of the capture positions P (shown in FIG. 5), the projection image of the elastic material 1 is captured, and the three-dimensional image of the elastic material 1 is observed. In such observing method, the three-dimensional image of the elastic material 1 can be observed in detail in a state approximate to the tire during running with the slip angle SA applied, therefore, the performance of the elastic material 1 can be accurately assessed.

In the present embodiment too, it is desirable that the elastic material 1 contains marker particles 52 (shown in FIG. 11) in order to emphatically capture the three-dimensional image 70 as in the former embodiment.

In the present embodiment, the slip angle SA is given to the elastic material 1 by rotating the support table 73, but it is not limited thereto. For example, it may be possible to set the slip angle SA to the elastic material 1 by rotating the second pusher 53 about a vertical axis.

Figure 19:
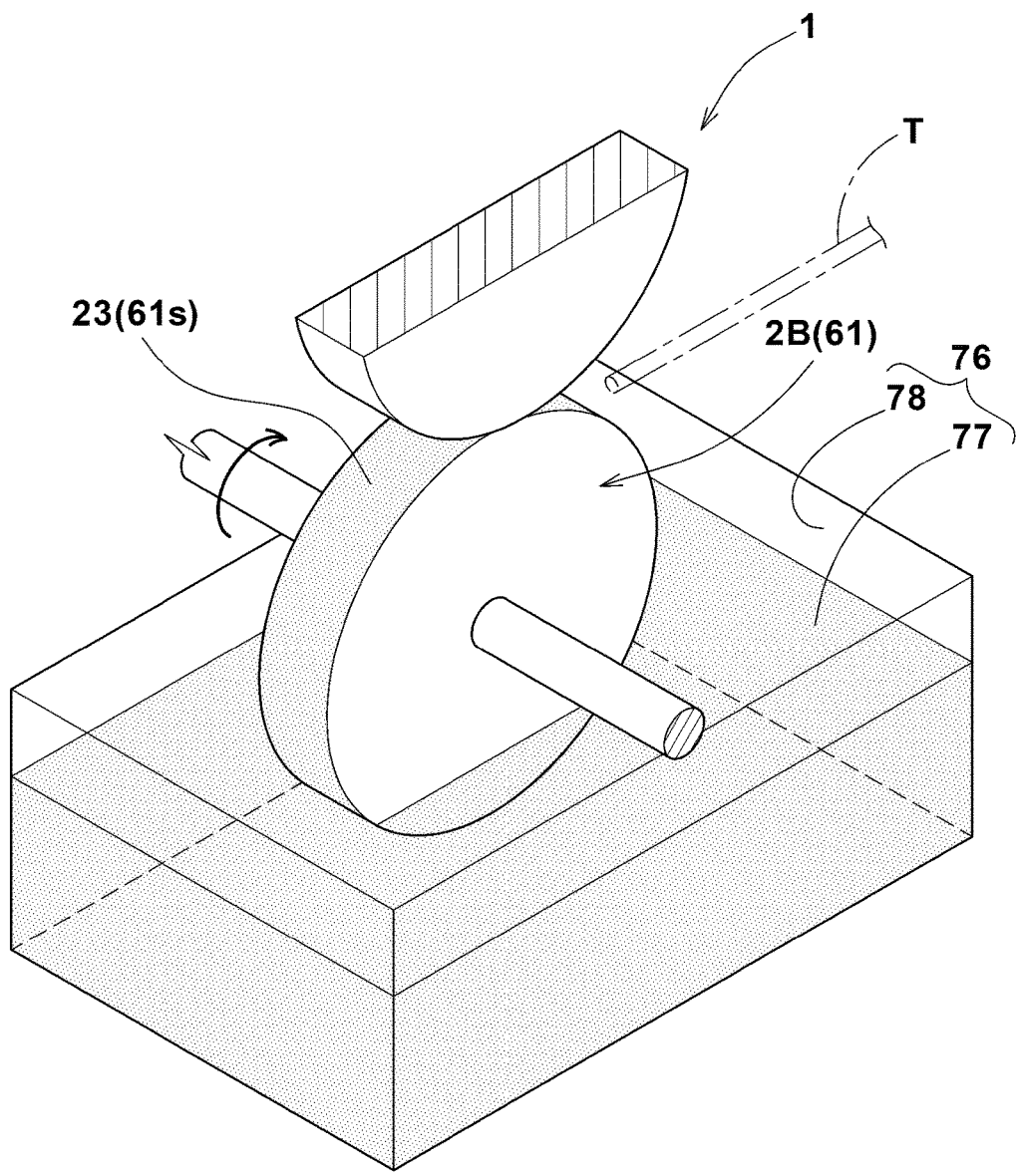
FIG. 19 A perspective view of the fluid supply means.

In the projection image capture apparatuses 2 in the above three embodiments, the elastic material 1 is pressed onto the dry contacted surface 23, but it is not limited thereto. For example, it may be possible to further include a fluid supply means for supplying a fluid toward the contact portion between the elastic material 1 and the contacted surface 23. FIG. 19 is a perspective view of the fluid supply means 76.

The fluid supply means 76 includes a water tank 78 in which the fluid 77 is stored. The water tank 78 is disposed beneath the drum 61 so that at least a part of the contacted surface 23 of the drum 61 is immersed in the fluid 77. Thereby, the fluid 77 is supplied to the contacted surface 23 of the drum 61 by rotating the drum 61 with the second rotating means 60 (shown in FIG. 16).

In the observing method using such projection image capture apparatus 2, a step of supplying the fluid 77 between the elastic material 1 and the contacted surface 23, is carried out in the deforming step S12, prior to (or at the same time) the step S121 or step S421 of pressing the elastic material 1 onto the contacted surface 23.

In the capturing step S14, therefore, it is possible to capture the projection image of the elastic material 1 with the fluid 77 interposed between the elastic material 1 and the contacted surface 23.

Figure 20:
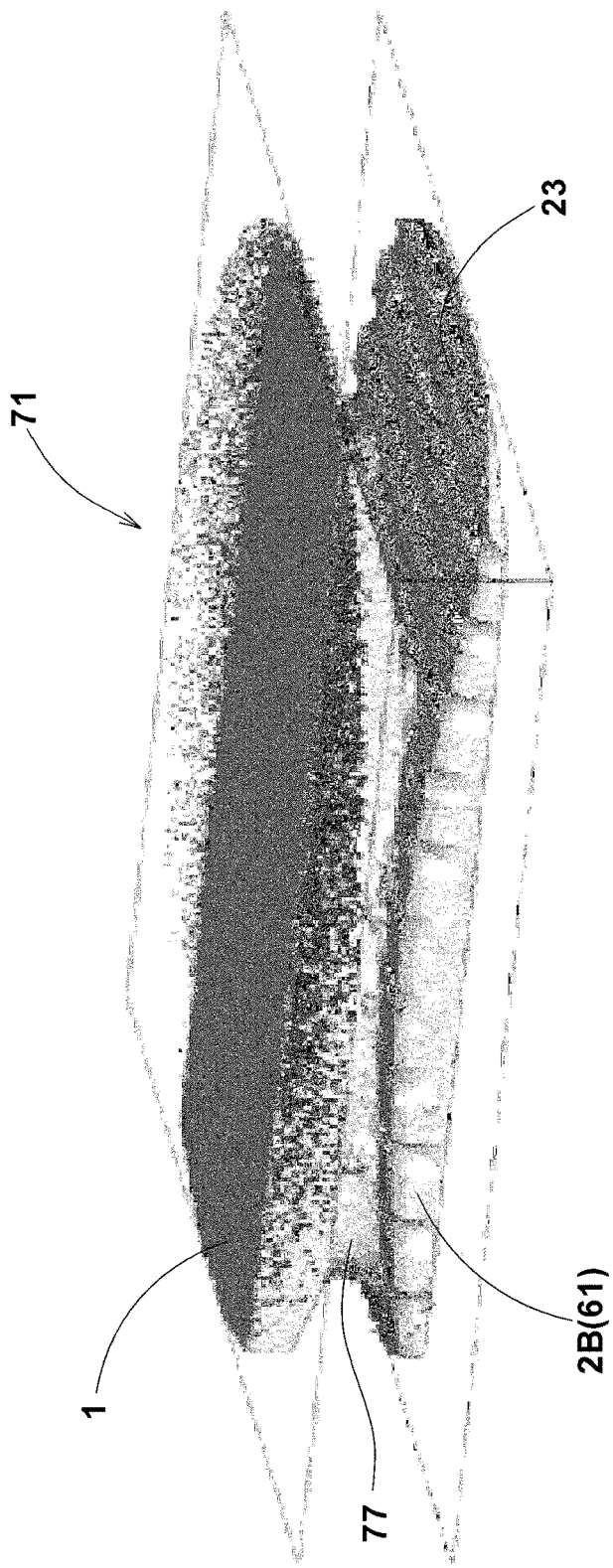
FIG. 20 A three-dimensional image of the elastic material and the contacted surface for which a fluid is supplied.

FIG. 20 is a three-dimensional image 71 of the elastic material 1 and the contacted surface 23 supplied with the fluid 77.

In the step S3 of such observing method, it is possible to evaluate wet performance of an actual tire for example. As the fluid 77, for example, water, oil, or a solution containing a contrast agent made up of a substance such as barium or iodine can be used.

In the present embodiment, the fluid 77 is supplied by the water tank 78 for storing the fluid 77, but it is not limited thereto. For example, it may be possible to supply the fluid 77 between the elastic material 1 and the contacted surface 23 through a tube T for supplying the fluid 77 as shown in FIG. 19 by an imaginary line.

Further, in the above described embodiments, the elastic material 1 is a cylindrical rubber material, but it is not limited thereto. The elastic material 1 may be, for example, a rubber material formed in a rectangular shape, or a tire for use in automobiles.

While detailed description has been made of especially preferable embodiments of the present invention, the present invention can be embodied in various forms without being limited to the illustrated embodiments.

WORKING EXAMPLES

Working Example A

According to the processing procedures shown in FIGS. 6, 7 and 8, with respect to an elastic material making linear reciprocating motions, a specific deformed state (a state in which the compressive deformation of the elastic material was maximum) of the elastic material was observed (working example 1).

Furthermore, according to the processing procedures same as those of working example 1, a specific deformed state of the elastic material containing marker particles was observed (working example 2).

In accordance with the processing procedures shown in FIGS. 6, 7 and 14, with respect to the elastic material being rotating, a specific deformed state of the elastic material (at a time point when a specific position of the outer peripheral surface of the elastic material came into contact with a specific position of the outer peripheral surface of the drum) was observed (working example 3).

In the working example 3, the fluid supply means was used. Common specifications of Working Examples 1 to 3 are as follows.

Elastic Material:
   outer diameter D1: 60 mm
   Width W1: 10 mm
Composition of Elastomeric material of Working Example 1 and Example 3:
   styrene-butadiene rubber (SBR): 100 parts by mass
   carbon black: 50 parts by mass
   sulfur: 2 parts by mass
   vulcanization accelerator: 1.5 parts by mass
Composition of Elastic material of Working Example 2:
   styrene-butadiene rubber (SBR): 0.89 parts by mass
   of carbon black: 50 parts by mass
   of sulfur: 2 parts by mass
   vulcanization accelerator: 1.5 parts by mass
   marker particles (alumina particles): 20 parts by mass
Details of materials making up elastic material are as follows:
   Rubber: Nippon neon Nipol iR2200
   Carbon black: Mitsubishi Chemical Corp. ISAF grade Sulfur: Tsurumi Chemical Industry Co., Ltd. powdered sulfur vulcanization accelerator: manufactured by Ouchi Shinko Chemical Industrial Co., N-tert-Butyl-2-benzothiazolesulfenamide alumina particles: Showa Denko KK CB-A40 average particle size: about 40 um Drum of Working Example 3:
outer diameter D3: 120 mm The three-dimensional image of Working Example 1 is shown in FIGS. 9 and 10.
The three-dimensional image of Working Example 2 is shown in FIG. 11.
The three-dimensional image of Working Example 3 is shown in FIG. 20.

In the observing method of Working Example 1, three-dimensional images of a specific deformed state (in the present embodiment, a state in which the compression deformation of the elastic material was maximum) was obtained.
Therefore, in the observing method of Working Example 1, it was possible to accurately evaluate the performance of the elastic material.

Further, in the observing method of Working Example 2, the three-dimensional image 51 was emphatically displayed in comparison with the observing method of Working Example 1. Therefore, in the observing method of Working Example 2, the performance of the elastic material was assessed accurately in comparison with the observing method of Working Example 1. Also, in the observing method of Working Example 3, the three-dimensional image of the elastic material rolling on the contacted surface was obtained.
Therefore, in the observing method of Working Example 3, the rolling performance of the elastic material was accurately assessed.

Working Example B

Figure 21:
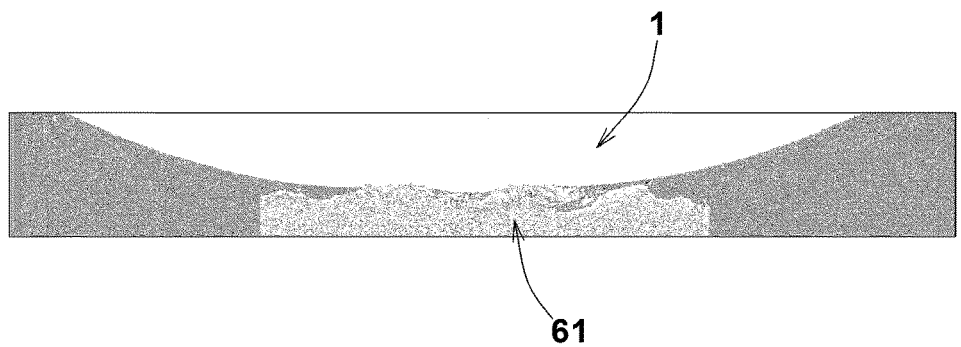
FIG. 21 A cross-section of the three-dimensional image constructed by Example 4.
Figure 22:
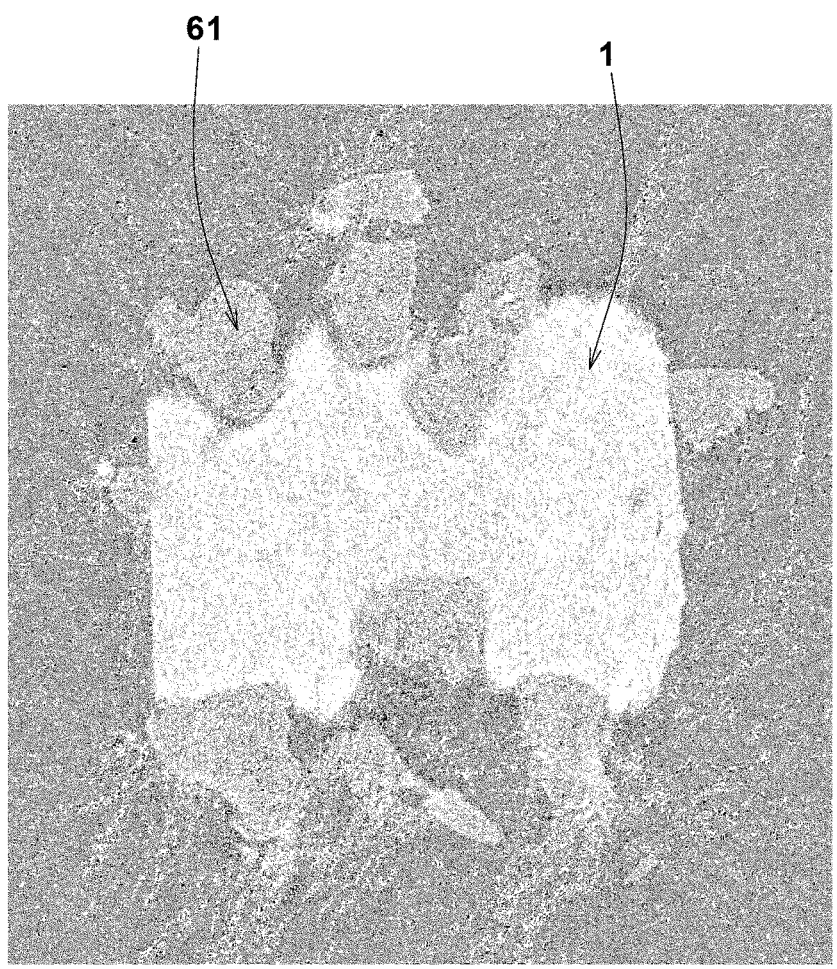
FIG. 22 An another cross-section of three-dimensional image constructed by Example 4.

According to the processing procedures shown in FIGS. 6, 7 and 18, with respect to the elastic material rolling with the given slip angle, a specific deformed state of the elastic material (a state in which the compressive deformation of the elastic material was maximum) was observed (working example 4). Specifications of the elastic material was the same as Working Example 3 above.
Test conditions were as follows.
The size of the drum:
outer diameter D3: 120 mm
width: 20 mm
load of elastic material: 20 N
slip angle of elastic material: 1 degree
FIG. 21 is a cross-section of the three-dimensional image constructed according to Working Example 4.
FIG. 22 is another cross-section of the three-dimensional image constructed according to Working Example 4.
As apparent from FIGS. 21 and 22, in the observing method of Working Example 4, a clear three-dimensional image of the elastic material in a state approximate to the tire during running with the given slip angle was obtained.
Therefore, in the observing method of Working Example 4, the performance of the elastic material could be accurately evaluated.

The invention claimed is:
1. A method for observing a deformation of an elastic material including rubber or elastomer, comprising:
a projection image obtaining step of capturing a projection image of at least a part of the elastic material, from a direction perpendicular to an axis passing through the elastic material, at each of a plurality of capture positions around the axis,
a three-dimensional image constructing step of constructing a three-dimensional image of said at least a part of the elastic material from the projection images respectively captured at said plurality of capture positions, and
a step of displaying the constructed three-dimensional image,
wherein:
the projection image obtaining step comprises:
deforming the elastic material in predetermined constant cycles by applying a cyclic load in the axis to the elastic material,
outputting capture signals respectively at same time points of said predetermined constant cycles, and
capturing the projection images at the capture positions from the respective perpendicular directions to the axis based on the respective capture signals.
2. The method for observing a deformation of an elastic material as set forth in claim 1, wherein
the deforming of the elastic material comprises linearly reciprocating the elastic material while being pressed onto a contacted surface.
3. The method for observing a deformation of an elastic material as set forth in claim 2, wherein
the capture signals are output by detecting a specific position in the linear reciprocating motion of the elastic material.
4. The method for observing a deformation of an elastic material as set forth in claim 2, which further comprise
a step of preparing the elastic material whose outer peripheral surface is formed into a circular shape, and
the projection image obtaining step comprises rotating the elastic material while pressing the outer peripheral surface of the elastic material onto the contacted surface.
5. The method for observing a deformation of an elastic material as set forth in claim 2, wherein in the capturing the projection images, capturing at least part of the contact portion between the elastic material and the contacted surface onto which the elastic material is pressed.
6. The method for observing a deformation of an elastic material as set forth in claim 2, wherein the projection image obtaining step further comprises supplying a fluid between the elastic material and the contacted surface onto which the elastic material is pressed.
7. The method for observing a deformation of an elastic material as set forth in claim 4, wherein the projection image obtaining step comprises setting a slip angle on the outer peripheral surface of the elastic material.
8. The method for observing a deformation of an elastic material as set forth in claim 4, wherein the capture signals are output by detecting a specific position in a rotational motion of the elastic material during rotating.
9. An apparatus for deforming an elastic material including rubber or elastomer and capturing projection images of the elastic material, comprising:
a deforming device for deforming the elastic material in predetermined constant cycles by cyclically pressing it onto a contacted surface,
a contact base having the contacted surface, a capture signal outputting device for outputting capture signals respectively at same time points of said predetermined constant cycles, and a capturing device for capturing projection images of at least a part of the elastic material, respectively, from a plurality of directions perpendicular to an axis passing through the elastic material, at a plurality of capture positions around the axis, based on the respective capture signals.

10. The apparatus for capturing a projection image of an elastic material as set forth in claim 9, wherein the deforming device comprises a first pusher to make the elastic material linearly reciprocate while pressing onto the contacted surface.

11. The apparatus for capturing a projection image of an elastic material as set forth in claim 9, wherein the elastic material has a circular outer peripheral surface, and the deforming device includes a second pusher for rotating the outer circumferential surface of the elastic material while pressing onto the contacted surface.

12. The apparatus for capturing a projection image of an elastic material as set forth in claim 9, which further comprises a fluid supply device for supplying a fluid to a contact portion between the elastic material and the contacted surface.

13. The apparatus for capturing a projection image of an elastic material as set forth in claim 9, wherein the elastic material contains marker particles.

14. The apparatus for capturing a projection image of an elastic material as set forth in claim 10, wherein the first pusher includes an electric motor having an output shaft that rotates, a conversion device for converting the rotational motion of the output shaft to a linear reciprocating motion, and a holder for holding the elastic material, connected to the conversion device.

15. The apparatus for capturing a projection image of an elastic material as set forth in claim 10, wherein the capture signal outputting device comprises a position detecting device for detecting a specific position in the linear reciprocating motion of the elastic material, and a pulse generator for outputting pulse signals as the capture signals based on detection signals of the position detecting device.

16. The apparatus for capturing a projection image of an elastic material as set forth in claim 11, wherein the second pusher comprises a holder for holding the elastic material, a first rotating device for rotating the elastic material, and an adjuster for changing the distance between the holder and the contacted surface.

17. The apparatus for capturing a projection image of an elastic material as set forth in claim 11, which further comprise a slip angle setting device for setting a slip angle on the outer circumferential surface of the elastic material to rotate on the contacted surface.

18. The apparatus for capturing a projection image of an elastic material as set forth in claim 11, wherein the contact base comprises a cylindrical drum, and the contacted surface is formed in the outer peripheral surface of the drum.

19. The apparatus for capturing a projection image of an elastic material as set forth in claim 11, which further comprises a second rotating device for moving the contacted surface.

20. The apparatus for capturing a projection image of an elastic material as set forth in claim 18, wherein a simulated road surface is formed in the contacted surface.

21. The apparatus for capturing a projection image of an elastic material as set forth in claim 20, wherein the capture signal outputting device comprises a first rotational position detecting device for detecting a specific position of the elastic material during rotating, a second rotational position detecting device for detecting a specific position of the contacted surface during moving, and a pulse generator for outputting a pulse signal based on a detection signal of the first rotational position detection device, and a detection signal of the second rotational position detecting device.

\* \* \* \* \*